United States Patent
Justin et al.

(10) Patent No.: US 12,128,155 B2
(45) Date of Patent: Oct. 29, 2024

(54) TISSUE EQUIVALENT TUBULAR SCAFFOLD STRUCTURE, AND METHODS OF PRODUCTION THEREOF

(71) Applicant: Cambridge Enterprise Limited, Cambridge (GB)

(72) Inventors: Alexander W. Justin, Cambridge (GB); Athina E. Markaki, Cambridge (GB)

(73) Assignee: CAMBRIDGE ENTERPRISE LIMITED, Cambridge (GB)

(*) Notice: Subject to any disclaimer, the term of this patent is extended or adjusted under 35 U.S.C. 154(b) by 435 days.

(21) Appl. No.: 17/602,237

(22) PCT Filed: Apr. 8, 2020

(86) PCT No.: PCT/EP2020/060068
§ 371 (c)(1),
(2) Date: Oct. 7, 2021

(87) PCT Pub. No.: WO2020/208094
PCT Pub. Date: Oct. 15, 2020

(65) Prior Publication Data
US 2022/0176015 A1     Jun. 9, 2022

(30) Foreign Application Priority Data
Apr. 9, 2019   (GB) .................................. 1905040

(51) Int. Cl.
*A61L 27/24* (2006.01)
*A61L 27/38* (2006.01)
(Continued)

(52) U.S. Cl.
CPC .............. *A61L 27/24* (2013.01); *A61L 27/38* (2013.01); *A61L 27/52* (2013.01); *A61L 27/56* (2013.01);
(Continued)

(58) Field of Classification Search
CPC .................................. A61L 27/38; A61L 27/24
See application file for complete search history.

(56) References Cited

U.S. PATENT DOCUMENTS 4,546,500 A * 10/1985 Bell .......................... A61F 2/06
623/921
4,814,120 A    3/1989 Huc et al.
(Continued)

FOREIGN PATENT DOCUMENTS

WO    2012/004564 A1    1/2012
WO    2018/136739 A1    7/2018

OTHER PUBLICATIONS

Brown et al., "Ultrarapid engineering of biomimetic materials and tissues: fabrication of nano- and microstructures by plastic compression", Advanced Functional Materials, Jan. 1, 2005, pp. 1762-1770, vol. 15, Wiley—V C H Verlag GMBH & CO. KGAA, DE.
(Continued)

*Primary Examiner* — Jacob T Minskey
*Assistant Examiner* — Wayne K. Swier
(74) *Attorney, Agent, or Firm* — HAMILTON, BROOK, SMITH & REYNOLDS, P.C.

(57) ABSTRACT

The present invention provides tissue equivalent scaffold structures and methods of production thereof. Such methods include providing a casting chamber comprising an elongate mould portion, axially disposing a lumen template within the elongate mould portion, and at least partly filling the casting chamber with a gel casting material comprising a matrix of fibrils or fibres and an interstitial fluid phase, such that a portion of the lumen template extends above the casting material. The fluid phase of the gel is allow to flow axially out of the elongate mould portion, in a restricted manner, thereby resulting in axial densification of the gel casting material to form a tissue equivalent tubular scaffold. Tissue equivalent scaffold structures according to the pres-
(Continued)

ent invention are able to support cell populations both within the walls and on the surface of the construct. They have enhanced mechanical strength due to increased collagen density, and are customisable in terms of luminal diameter and wall thickness. They may find application in tubular tissue engineering.

20 Claims, 17 Drawing Sheets

(51) Int. Cl.
  *A61L 27/52*    (2006.01)
  *A61L 27/56*    (2006.01)
  *B29C 39/10*    (2006.01)
  *B29C 39/26*    (2006.01)
  *B29K 105/00*    (2006.01)
  *B29L 31/00*    (2006.01)

(52) U.S. Cl.
  CPC .............. *B29C 39/10* (2013.01); *B29C 39/26* (2013.01); *B29K 2089/00* (2013.01); *B29K 2105/0061* (2013.01); *B29L 2031/753* (2013.01)

(56) References Cited

U.S. PATENT DOCUMENTS

| | | | |
|---|---|---|---|
| 5,256,418 | A | 10/1993 | Kemp et al. |
| 5,292,802 | A | 3/1994 | Rhee et al. |
| 2008/0131473 | A1* | 6/2008 | Brown ................. A61L 27/24 435/1.1 |
| 2017/0022464 | A1* | 1/2017 | Novak ............... G01N 33/5005 |
| 2017/0312780 | A1* | 11/2017 | Schwartz ................. B05D 1/32 |
| 2018/0185553 | A1 | 7/2018 | Voytik-Harbin et al. |
| 2018/0346862 | A1* | 12/2018 | Bandini ................ C12M 25/14 |

OTHER PUBLICATIONS

PCT International Search Report and Written Opinion for International Application No. PCT/EP2020/060068 entitled "Tissue Equivalent Tubular Scaffold Structure, and Methods of Production Thereof," mailed on Jul. 22, 2020; Consisting of 16 pages.
Langer, et al. "Advances in tissue engineering." Journal of Ped. Surgery 51 (2016): pp. 8-12.
Sampaziotis, et al. "Reconstruction of the mouse extrahepatic biliary tree using primary human extrahepatic cholangiocyte organoids." Nature medicine 23.8 (2017): pp. 954-960.
Hori, et al. "Tissue engineering of the small intestine by acellular collagen sponge scaffold grafting." The International Journal of Artificial Organs 24.1 (2001): pp. 50-54.
Grikscheit, et al. "Tissue-Engineered Large Intestine Resembles Native Colon With Appropriate In Vitro Physiology and Architecture." Annals of Surgery 238.1 (2003): pp. 35-41.
Poghosyan, et al. "Esophageal tissue engineering: Current status and perspectives." Journal of Visceral Surgery 153 (2016): pp. 21-29.
Atala, "Tissue engineering for the replacement of organ function in the genitourinary system." American Journal of Transplantation 4 (Suppl. 6) (2004): pp. 58-73.
O'Leary, et al. "Respiratory Tissue Engineering: Current Status and Opportunities for the Future." Tissue Engineering Part B: Reviews 21.4 (2015): pp. 323-345.
Seifu, et al. "Small-diameter vascular tissue engineering." Nature Reviews Cardiology 10 (2013): pp. 410-421.
Huang, et al. "Engineering of arteries in vitro." Cellular and Molecular Life Sciences 71 (2014): pp. 2103-2118.
Wangensteen, et al. "Collagen Tube Conduits in Peripheral Nerve Repair: A Retrospective Analysis." Hand 5 (2010): pp. 273-277.
Williams, et al. "New metrics for the Lancet Standing Commission on Liver Disease in the UK" Lancet 389(10083): pp. 2053-2080, (2017).
Murray et al., "AASLD Practice Guidelines: Evaluation of the Patient for Liver Transplantation" Hepatology, vol. 41, No. 6, pp. 1407-1432, (2005).
Skaro, et al., "The impact of ischemic cholangiopathy in liver transplantation using donors after cardiac death: The untold story" Surgery, vol. 146, No. 4, pp. 543-553, (2009).
Justin, et al. "Advances in the generation of bioengineered bile ducts." Biochimica et Biophysica Acta (BBA)-Molecular Basis of Disease 1864 (2018): pp. 1532-1538.
Macchiarini, et al. "Clinical transplantation of a tissue-engineered airway." Lancet 372 (2008): pp. 2023-2030.
Ghezzi, et al. "Immediate production of a tubular dense collagen construct with bioinspired mechanical properties." Acta Biomaterialia 8 (2012): pp. 1813-1825.
Loy, et al. "Rotation-based technique for the rapid densification of tubular collagen gel scaffolds." Biotechnology Journal 11 (2016): pp. 1673-1679.
L'Heureux, et al. "Human tissue-engineered blood vessels for adult arterial revascularization." Nature Medicine 12.3 (2006): pp. 361-365.
Hoenig, et al. "Tissue-Engineered Blood Vessels: Alternative to Autologous Grafts?" Arterioscler Thromb Vasc Biol. 25 (2005): pp. 1128-1134.
Quint, et al. "Decellularized tissue-engineered blood vessel as an arterial conduit." Proceedings of the National Academy of Sciences vol. 108, No. 22 (2011): pp. 9214-9219.
Boland, Eugene D., et al. "Electrospinning collagen and elastin: preliminary vascular tissue engineering." Front Biosci9.1422 (2004): e32.
Nakamura, Tasuo, et al. "Experimental study on the regeneration of peripheral nerve gaps through a polyglycolic acid—collagen (PGA-collagen) tube." Brain Research 1027.1-2 (2004): 18-29.
Song, H-H. Greco, et al. "Vascular tissue engineering: progress, challenges, and clinical promise." Cell stem cell 22.3 (2018): 340-35.
Martin, Laura Y., et al. "Tissue engineering for the treatment of short bowel syndrome in children." Pediatric research 83.1-2 (2018): 249.
Udelsman, Brooks, Douglas J. Mathisen, and Harald C. Ott. "A reassessment of tracheal substitutes-a systematic review." Annals of cardiothoracic surgery 7.2 (2018): 175.
Goh, Cindy Siaw-Lin, et al. "Large animal models for long-segment tracheal reconstruction: a systematic review." Journal of Surgical Research 231 (2018): 140-153.
Arakelian, Lousineh, et al. "Esophageal tissue engineering: from bench to bedside." Annals of the New York Academy of Sciences 1434.1 (2018): 156-163.
Justin, Alexander W.,et al. "Multi-casting approach for vascular networks in cellularized hydrogels." Journal of the Royal Society Interface 13.125 (2016): 20160768.
Golden, Andrew P., and Joe Tien. "Fabrication of microfluidic hydrogels using molded gelatin as a sacrificial element." Lab on a Chip 7.6 (2007): 720-725.
Wimmer, Reiner A., et al. "Human blood vessel organoids as a model of diabetic vasculopathy." Nature (2019).
McCoy, Michael G., et al. "Collagen Fiber Orientation regulates 3D Vascular Network Formation and Alignment." ACS Biomaterials Science & Engineering 4.8 (2018): 2967-2976.
Chwalek, Karolina, et al. "Glycosaminoglycan-based hydrogels to modulate heterocellular communication in in vitro angiogenesis models." Scientific reports 4 (2014): 4414.
Micol, Lionel A., et al. "High-density collagen gel tubes as a matrix for primary human bladder smooth muscle cells." Biomaterials 32.6 (2011): 1543-1548.

\* cited by examiner

TISSUE EQUIVALENT TUBULAR SCAFFOLD STRUCTURE, AND METHODS OF PRODUCTION THEREOF

RELATED APPLICATIONS

This application is the U.S. National Stage of International Application No. PCT/EP2020/060068, filed Apr. 8, 2020, which designates the U.S., published in English, and claims priority under 35 U.S.C. § 119 or 365(c) to Great Britain Application No. 1905040.0, filed Apr. 9, 2019. The entire teachings of the above applications are incorporated herein by reference.

FIELD

The present invention relates to tissue equivalent scaffold structures and methods of production thereof. Particularly, although not exclusively, it relates to human-sized tissue equivalent tubular scaffolds and methods of production thereof.

BACKGROUND

One of the standard paradigms of tissue engineering is the seeding of scaffolds with patient-derived cells and subsequent transplantation as replacement for diseased tissues and organs [1].

Decellularization is an established technique for obtaining tissue engineering scaffolds which maintain the extracellular matrix and the fine structure of the tissue or organ. Many tubular structures have been investigated using this technique, including trachea [15] and arteries [20]. A harvested scaffold can then be seeded with a patient's cells to regain functionality prior to implantation as a replacement tissue. However, decellularization as a technique is limited by donor availability, extensive materials processing, and risks associated with remaining biological material, including the risk of transmitting pathogens [21]. Further, the patient specificity of decellularized scaffolds and variation between donor sources (e.g. age, species, sex) lead to variation in biological and mechanical properties [8]. Other methods for tube formation include using an intraperitoneal graft, which induces an inflammatory response and yields a fibromuscular tube, which can be extracted from the animal and used as an artificial artery [19].

Due to the limitations of using decellularized materials as tissue scaffolds, much work has been done on production of tissue equivalent scaffolds/structures. For example, natural polymers are commonly used as a scaffold material, including standard un-densified collagen gel. However, these are often mechanically weak to use for many structures, such as tubes, in a clinical setting. Furthermore, their rapid degradation in vivo leads to a loss of mechanical strength. While crosslinking techniques offer more control over mechanical properties, they can negatively affect cellular interactions.

Several methods have been investigated for forming structures such as tubes, which have all been explored in the context of clinical studies. These method include: formation of self-assembled cell sheets, which are rolled into tubes; natural polymeric scaffolds (e.g. collagen, elastin, fibrin); synthetic polymeric scaffolds (e.g. polyglycolide (PGA), polylactic acid (PLA), polycaprolactone (PCL)); and decellularized scaffolds, in which similar tissue (allogenic, xenogenic) is stripped of cells and reseeded with the patient's own cells [8]. The use of collagen as a scaffold material is often overlooked due to the weak mechanical properties of standard collagen gel, despite being a gold standard on which to grow various cell types. However, it is known to densify collagen into e.g. sheets and tube, which may have greater application as tissue-equivalent structures. The standard method for "plastic compression" of collagen involves placing a collagen gel on a nylon (hydrophilic) membrane and paper blot. By loading the gel from above, one forces the water from the gel, which densifies and aligns the collagen fibrils [24]. One known method uses this standard plastic compression to form a densified collagen sheet, which is subsequently rolled to form a tube [16]. Another method wraps a nylon membrane and paper towels around a collagen gel and suspends it to allow water extraction [23]. Another method involves slowly rotating a standard collagen gel to expel water and thus form a thin-walled, densified collagen tube [17]. In this study, they were also able to make thin-walled bifurcating tubes [17].

Collagen has also been used to form tissue-equivalent structures using lyophilisation techniques (i.e. freeze-drying). For example, porous collagen sponges have been implanted around silicone tube stent which, once the stent was removed endoscopically, produced a viable replacement for a section of intestine [3]. Tubes have been formed using electrospinning to form vascular grafts and can be made from collagen [21] and PGA-collagen hybrid tubes have been formed as nerve conduits [22].

Mouse-sized densified collagen tubes for use as a replacement for the common bile duct have been fabricated in the literature [2] by a technique using a 3D printed chamber consisting of a funnel piece, and a base plate having a metallic wire mounted centrally thereon. In this process, the chamber is filled with a collagen gel solution to above the level of the metallic wire. As the collagen solution gels within the chamber, the surface of the collagen gel catches on the top of the central metal wire, which stops the collagen gel surface dropping any further. Instead, as the collagen gel loses water, it densifies radially inwards onto the central wire, producing a thin layer of collagen and thus forming a tubular structure within the funnel-shaped section of the mould. The tube is then removed from the chamber, trimmed for excess collagen, and cut to the required length. The resulting constructs have small inner diameters (e.g. 250 µm), and are thin-walled (i.e. 50-250 µm thick), formed mostly through evaporation along the length of tube (i.e. radial densification). Due to the evaporative nature of the water removal, the tubes have a low degree of reproducibility; for example the wall thickness is much harder to predict as it depends upon the degree of water removal (i.e. drying) of the collagen gel.

However, the above method ('mouse-sized method') is incapable of producing 'thick-walled' constructs (e.g. >0.5 mm wall thickness) which may be suitable for human applications due to the large volume of un-densified collagen gel that would be required at the start and thus the volume of water that would have to be removed via evaporation.

U.S. patent application Ser. No. 15/851,732, 5 Jul. 2018 describes absorption of water from a collagen gel into a porous polyethylene rod in the lumen [25]. A syringe, with mounted porous polyethylene rod at the centre, is filled with collagen and by applying a vacuum to the porous rod, water is removed from the collagen gel [25]. In each of these methods, the direction of densification is radially inwards towards the central mandrel.

U.S. Pat. No. 4,814,120. 21 Mar. 1989 describes use of concentrating agents which cause the mass transfer of water from the collagen gel, so as to form a densified collagen gel of structures including tubes [27].

U.S. Pat. No. 5,292,802. 8 Mar. 1994 describes a method in which collagen is covalently bound to synthetic polymers (e.g. PGA), which is formed into a tube and dehydrated, for use in vascular surgery [28].

However, many of these methods are complicated, and do not provide for facile production of human-sized tissue equivalent structures.

Accordingly, it is desired to provide a method for production of human-sized tissue equivalent structures.

The fabrication of human-sized tissue equivalent structures such as collagen tubes may find application as replacement tissues in a range of fields including gastrointestinal (bile duct [2], small [3] and large [4] intestine, oesophagus [5, 33]), genitourinary [6, 23] (ureter, urethra), respiratory [7] (trachea, bronchi), cardiovascular (coronary artery and small diameter vessels [8]), and peripheral nerve repair [10] research. Together, these represent a number of surgical procedures, treating a large range of human diseases.

The present invention has been devised in light of the above considerations.

SUMMARY

The present inventors have developed a method for the production of tubular scaffolds that match the size of human tubular tissue structures. These tubular scaffolds are useful for example as replacement tissues for medical applications.

Accordingly, in a first aspect, the present invention provides a method of making a tissue equivalent tubular scaffold comprising:
  providing a casting chamber comprising an elongate mould portion;
  providing a lumen template axially disposed within the elongate mould portion;
  at least partly filling the casting chamber with a gel casting material comprising a fluid phase, such that a portion of the lumen template extends above the casting material; and
  allowing restricted axial flow of the fluid phase of the gel casting material out of the elongate mould portion, thereby densifying gel casting material within the elongate mould portion to form the tissue equivalent tubular scaffold.

These steps may take place in any appropriate order. For example, the step of providing a lumen template disposed within the casting chamber may be performed before or after the step of at least partly filling the casting chamber with a casting material to a predetermined fill level.

Restricted axial flow here means a flow rate less than a hypothetical flow rate in the absence of any restriction. The step of allowing restricted axial flow of the fluid phase of the gel casting material out of the elongate mould portion may include provision of a flow-limiting member at an outlet of the elongate mould portion. The flow-limiting member may be e.g. a disc or plate arranged to restrict the area of an outlet of the elongate mould portion. The size and shape of the flow-limiting member may be selected to thereby reduce the effective area of an outlet of the elongate mould portion. The effective area reduction may be 50% or more, 60% or more, 70% or more, 80% or more, 90% or more, or 95% or more. Preferably the effective area reduction is not greater than 99.9%.

The flow-limiting member may be non-porous and/or impermeable. The flow-limiting member may be formed from any suitable material, e.g. a metal (including but not limited to stainless steel, or anodised aluminium), a glass and/or a synthetic polymer (including but not limited to polystyrene, nylon, acrylic (PMMA), or Teflon (PTFE)), or any combination of these materials. Polymeric materials may be preferred due to their low cost and ease of manufacture.

Alternatively or additionally, allowing restricted axial flow of the fluid phase of the gel casting material out of the elongate mould portion may be achieved by providing a casting chamber comprising an elongate mould portion having a closed end, wherein at least part of the closed end of the elongate mould portion of the casting chamber is porous. Axial flow of the fluid phase of the gel casting material out of the elongate mould portion can then occur via the porous end part of the elongate mould portion. In such an arrangement, the porous end part of the elongate mould portion can be considered to be an outlet of the elongate mould portion.

Accordingly, the present invention provides a method of making a tissue equivalent tubular scaffold comprising:
  providing a casting chamber comprising an elongate mould portion having a closed end, wherein at least part of the closed end of the elongate mould portion of the casting chamber is porous;
  providing a lumen template axially disposed within the elongate mould portion;
  at least partly filling the casting chamber with a gel casting material comprising a fluid phase, such that a portion of the lumen template extends above the casting material; and
  allowing axial flow of the fluid phase of the gel casting material out of the porous end part of the elongate mould portion, thereby densifying gel casting material within the elongate mould portion to form the tissue equivalent tubular scaffold.

These steps may take place in any appropriate order. For example, the step of providing a lumen template disposed within the casting chamber may be performed before or after the step of at least partly filling the casting chamber with a casting material to a predetermined fill level.

In the methods described herein, the lumen template extends above the top surface of the casting material. This prevents the casting material from being held in position by the top of the lumen template and allows the level of the casting material to drop as the fluid phase of the casting material passes through the elongate mould portion in an axial direction (i.e. along the length of the elongate mould portion) and not in a radial direction (i.e. across the width of the elongate mould portion)

In methods according to the present invention, the fluid phase of the gel casting material axially flows out of the elongate mould portion e.g. via the porous end portion or outlet, whilst another phase of the gel casting material (e.g. a matrix of fibrils or fibres) is retained within the casting chamber, thereby increasing the density of (i.e. densifying) the gel casting material within the elongate mould portion. Because the fluid phase is removed by active flow of the fluid phase of the casting material out of the casting chamber rather than by e.g. passive evaporation, relatively large amounts of the fluid phase may be removed from the gel casting material, thereby allowing for densification of larger volumes of casting material to thereby form larger scaffold structures than in methods that rely mainly or solely on evaporation of a fluid phase of a casting material. Furthermore, the densification process (which occurs primarily by axial densification) results in a high density of remaining casting material (e.g. fibrils or fibres), thus providing a scaffold having comparable mechanical strength to native tissue.

One additional advantage provided by embodiments of the present invention where the provided casting chamber comprises an elongate mould portion having a closed end, wherein at least part of the closed end of the elongate mould portion of the casting chamber is porous, are that the porous end part provides an anchoring surface for the gel casting material, due to infiltration of fibre or fibrils of the gel casting material into surface pores of the porous end part. For example, where a porous membrane forms the porous end part, the gel casting material can infiltrate into surface pores of the membrane, thereby 'anchoring' the gel casting material to the membrane during densification. Providing this 'anchoring' can prevent the gel casting material from retracting upwardly during densification, which may prematurely stop the densification process. Furthermore, providing an elongate mould portion having a closed end also reduces the occurrence of air bubbles entering the casting chamber prior to and during densification, thereby resulting in improved casting and densification of the gel casting material.

In some arrangements, at least a part of the closed end of the elongate mould portion may be substantially non-porous and impermeable. Additionally or alternatively, a substantially non-porous and impermeable member may be disposed adjacent the porous end part of the elongate mould portion within the casting chamber, or externally to the casting chamber. In this way, the non-porous and impermeable member, or non-porous and impermeable portion of the closed end of the elongate mould portion may act to partially restrict flow of a fluid out of the porous end part of the elongate mould portion as compared with a similar arrangement in which no non-porous and impermeable member, or no non-porous and impermeable portion of the elongate mould portion is present. Furthermore, provision of a non-porous and impermeable portion or member may reduce surface roughness of an end portion of the tissue equivalent tubular scaffold formed by densification of the gel casting material within the elongate mould portion, because the gel casting material does not penetrate into the non-porous and impermeable portion or member during densification.

The non-porous and impermeable member may be a plate or disk. Any suitable material may be used, e.g. a metal (including but not limited to stainless steel, or anodised aluminium), a glass and/or a synthetic polymer (including but not limited to polystyrene, nylon, acrylic (PMMA), or Teflon (PTFE)), or any combination of these materials. Polymeric materials may be preferred due to their low cost and ease of manufacture.

The size and shape of the non-porous and impermeable member may be selected to thereby reduce the effective area of the porous end part of the elongate mould portion (when viewed axially in a direction along the length of the elongate mould portion). The effective area reduction may be 50% or more, 60% or more, 70% or more, 80% or more, 90% or more, or 95% or more. Preferably the effective area reduction is not greater than 99.9%. In one arrangement, the non-porous and impermeable member comprises a disc arranged approximately centrally within the elongate mould portion, thereby reducing the effective area of the porous end part of the elongate mould portion to a concentric ring around the edges of the disc. By reducing the effective area of the porous end part of the elongate mould portion, axial flow of the fluid phase of the gel casting material out of the porous end part of the elongate mould portion may be restricted, thereby allowed greater control over densification of the gel casting material.

In an alternative arrangement, the non-porous and impermeable member comprises a disc arranged externally to the casting chamber, and being of a larger diameter than the elongate mould portion. The fluid phase of the gel casting material then flows out of the elongate mould portion via a small gap formed between the casting chamber and the non-porous and impermeable member.

The resulting tubular scaffold may comprise a tube wall surrounding an internal lumen. The outer size and shape of the tube wall may be substantially defined by the size and shape of an inner surface of the elongate mould portion of the casting chamber. Preferably, the resulting tubular scaffold is the approximate size of human tubular tissue structures. Accordingly, the elongate mould portion of the casting chamber may be substantially cylindrical, and may have an average inner diameter of from about 2 mm to about 40 mm. For example, the average inner dimeter of the elongate mould portion may be 2 mm or more, 3 mm or more, 4 mm or more, 5 mm or more, 10 mm or more or 20 mm or more. The average inner diameter of the elongate mould portion may be 40 mm or less, 30 mm or less or 20 mm or less. The resulting tubular scaffold may have a corresponding average outer diameter of from about 2 mm to about 40 mm. For example, the average outer dimeter of the tubular scaffold may be 2 mm or more, 3 mm or more, 4 mm or more, 5 mm or more, 10 mm or more or 20 mm or more. The average outer diameter of the tubular scaffold may be 40 mm or less, 30 mm or less or 20 mm or less.

The material of the lumen template is not particular limited. The lumen template may comprise e.g. a metal (including but not limited to stainless steel, or anodised aluminium), a glass, a biological polymer (including but not limited to gelatin) and/or a synthetic polymer (including but not limited to nylon, acrylic (PMMA), or Teflon (PTFE)), or any combination of these materials. Polymeric materials may be preferred due to their low cost and ease of manufacture. In some embodiments, the lumen template comprises a gel, for example a gelatin gel.

The size and shape of the lumen of the tubular scaffold may be substantially defined by the outer size and shape of the lumen template. The size and shape of the lumen template is not particularly limited, although is preferably elongate. The lumen template may comprise e.g. a rod or a bifurcated rod, a wire or a tube. In some arrangements, the lumen template may comprise a plurality of template members. For example, the lumen template may comprise a plurality of wires, each having a diameter of between e.g. 20-200 µm, the wires optionally being bundled together. Such an arrangement may find particular applicability for use as e.g. nerve/neuronal guides.

The lumen template may have an average outer diameter of from about 0.01 mm to about 20 mm. For example, the average outer diameter of the lumen template may be 0.01 mm or more, 0.1 mm or more, 0.5 mm or more, 1 mm or more, 5 mm or more, or 10 mm or more. The average outer diameter of the lumen template may be 20 mm or less or 10 mm or less. The resulting tubular scaffold may have an average lumen diameter of about 0.01 mm to about 20 mm. For example, the average lumen diameter may be 0.01 mm or more, 0.1 mm or more, 0.5 mm or more, 1 mm or more, 5 mm or more, or 10 mm or more. The average lumen diameter may be 20 mm or less or 10 mm or less.

The wall thickness of the tubular scaffold may be substantially defined by the distance between an inner wall of the elongate mould portion, and an outer surface of the lumen template. The average distance between an inner wall of the elongate mould portion, and an outer surface of the lumen template may be from about 0.3 mm to about 20 mm. The resulting tubular scaffold may have an average tube wall thickness of from about 0.3 mm to about 20 mm, although there is potentially no upper limit to the possible wall thicknesses which it is possible to produce using the methods of the invention. Preferably, the tubular scaffold is a 'thick-walled' tube, i.e. has an average wall thickness of 0.5 mm or greater.

Human-sized is here used to refer to structures that are substantially the same size as equivalent natural human tissue. For example, a human biliary duct is typically a tube having a diameter of about 7 mm, and a wall thickness of about 0.5-1 mm. However, tissue structures on a wide range of length scales are found throughout the human body.

Thick-walled tubular scaffolds may resemble native tissue conduits in humans (e.g. the bile duct), in particular as they may have a wall thickness similar to that of such native tissue conduits. Furthermore, they may provide a significantly greater mechanical strength, in the axial, circumferential and/or radial directions, than a thin-walled equivalent structure (e.g. a structure having the same lumen size but with wall thickness<0.5 mm). Human-sized tissue conduits have a larger inner diameter than a small animal (e.g. mouse, rat) and so may require a proportionately thicker wall to support an increased volumetric flow rate. Further, a thick-walled tube may have increased resistance to leaking through any particular degradation process (e.g. chemical degradation, cellular remodelling) relative to a thin-walled tube, as a greater volume of collagen would have to be broken down before failing. Further, thick-walled tubes may provide a greater degree of mechanical strength to suture to adjoining tissue. Further, as the direction of densification is axial, scaffolds produced according to this method will not have a seam along their length in an axial direction, i.e. such scaffolds will be seamless. Seamless scaffolds are advantageous because presence of a seam can weaken the scaffold both mechanically and increase the rate of failure from chemical degradation.

Finally, a thick-walled tubular scaffold may enable the inclusion of vascular networks of a range of sizes. Accordingly, the tissue equivalent tubular scaffold may comprise one or more vascular structures e.g. having typical feature diameters from 250 μm to greater than 1 mm. The tissue equivalent tubular scaffold may comprise a vascular network. Such vascular structures or vascular networks may be fabricated via materials processing methods and/or cellular approaches. Such vascular structures or vascular networks could be perfused in vitro. A thin-walled construct (e.g. with 250 μm thick walls) may be limited to capillary-sized structures (i.e. 5-20 μm). Further details of how to provide such vascular networks using materials processing methods may be found in e.g.:

Alexander W. Justin, Roger A. Brooks, and Athina E. Markaki. "Multi-casting approach for vascular networks in cellularized hydrogels." *Journal of The Royal Society Interface* 13.125 (2016): 20160768. This paper discloses formation of vascular networks with typical feature diameters from >1 mm to 250 μm, and with complex, hierarchical, and 3D vascular architecture.

Golden, Andrew P., and Joe Tien. "Fabrication of microfluidic hydrogels using molded gelatin as a sacrificial element." *Lab on a Chip* 7.6 (2007): 720-725.

As regards cellular approaches, co-culture systems of endothelial and supporting cell types, or vascular organoids, may be used to produce suitable-sized vessels. For example, a micro-vasculature network can be produced by mixing endothelial cells and a supporting cell type (i.e. a cellular co-culture system), such as fibroblasts, pericytes, or mesenchymal stem/stromal cells. These may interact with one another to form capillary-sized vessels. This process can be accelerated or modified by the addition of growth factors, such as vascular endothelial growth factors (VEGF) including VEGFA-121,165,189, VEGFB, basic fibroblast growth factor (bFGF, also known as FGF2), and stromal derived factor (SDF-1a, also known as CXCL12).

This is shown for example in work by Wimmer, Reiner A., et al. "Human blood vessel organoids as a model of diabetic vasculopathy." Nature (2019), and also in McCoy, Michael G., et al. "Collagen Fiber Orientation regulates 3D Vascular Network Formation and Alignment." *ACS Biomaterials Science & Engineering* 4.8 (2018): 2967-2976.

The length of the resultant tubular scaffold is not particularly limited. The length is dependent on the starting volume and concentration of the gel casting material, and the relative diameters of the elongate mould portion and lumen template which thereby define the wall thickness of the tubular scaffold. Assuming the same volume of casting material and identical densification, a smaller wall thicknesses will lead to longer tubular scaffolds as less casting material is needed per unit length, as compared with large wall thicknesses, which have a higher volume of casting material per unit length. The preferred length depends on the application for which the scaffold is intended. For example, whilst tubular scaffolds for use in biliary research may require a length of only around 15 mm, tubular scaffolds for use in e.g. intestinal research may require a length of e.g. 1 m or more. Typical lengths suitable for use in a range of applications may be from e.g. 1 cm and 30 cm. For example, the tubes may have a length of about 2 cm, about 3 cm, about 4 cm, about 5 cm, about 10 cm, about 15 cm, about 20 cm, about 25 cm or about 30 cm.

A gel is a material comprising a matrix of fibrils or fibres and an interstitial fluid phase. Preferably the fibrils or fibres are formed from a biocompatible material. Gels are formed by the coalescence and elongation of fibrils, as the fibrils form a continuous network around the aqueous interstitial fluid which originally held the monomers. The gel may comprise a hydrogel, wherein the interstitial fluid phase comprises water. For example, triple helical collagen monomers may be initially dissolved in dilute acid and then induced to polymerise (aggregate) to fibrils (e.g. at neutral pH and by raising the ionic content at temperatures between about 4° C. and about 37° C.). As the fibrils polymerise, there is a phase change and the solid network of fibrils 'supports' the remaining interstitial liquid in approximately the same volume and shape—i.e. it gels. Alternatively, the gel may comprise an alcogel, wherein the interstitial fluid phase comprises an alcohol. The concentration of fibrils or fibres in the interstitial fluid phase may be selected as appropriate, however fibres/fibrils may be present in an amount of e.g. 1 mg/ml to 10 mg/ml, more preferably 2.5 to 7.5 mg/ml, most preferably about 5 mg/ml. Gels having concentrations within these ranges may offer superior casting properties. If the gel concentration is too high, bubbles may form during casting, or be trapped within the casting chamber during the step of partly filling the casting chamber with the gel casting material. If the gel concentration is too low, effective densification of the gel casting material may be difficult to achieve, as large pores within the gel casting material may allow for very fast removal of the liquid phase of the gel casting material during densification, leading to the formation of weaker tubes, although it may nevertheless be possible to achieve effective densification even at low gel concentrations by providing increased restriction on axial fluid flow of the liquid phase of the gel casting material out of the casting chamber. For example where the casting chamber comprises an elongate mould portion having a closed end, wherein at least part of the closed end of the elongate mould portion of the casting chamber is porous, increased restriction on axial fluid flow (and thereby effective densification even at low gel concentrations) may be provided by selecting an appropriately small average pore size for the porous elongate mould portion, e.g. 0.025 µm.

The methods described herein may therefore additionally include a step of allowing gelation of a solution to form the gel casting material. This may take place before or after the step of at least partly filling the casting chamber with a casting material: the gel casting material may, in some embodiments, be formed in-situ within the casting chamber from a solution (a gel precursor solution). In other words, the step of at least partly filling the casting chamber with a gel casting material may include the sub-steps of: at least partly filling the casting chamber with a gel precursor solution, and allowing the gel precursor solution to gel to thereby form a gel casting material.

Any hydrated polymer material may be suitable for use in a gel described herein, including naturally occurring polymers, for example proteins, such as silk, fibrin, fibrinogen, fibronectin, laminin, elastin, albumin or collagen (e.g. collagen type I), glycoproteins such as fibronectin, or polysaccharides such as glycosaminogylcans [38], chitin, cellulose, or methylcellulose. In some preferred embodiments, the scaffold fibrils or fibres of the gel casting material are made from collagen (i.e. the gel casting material may be a collagen gel). Native fibril forming collagen types are preferred including collagen types are I, II, III, V, VI, IX and XI and combinations of these (e.g. I, III V or II, IX, XI). For example, collagen type I may be used as the scaffold fibrils or fibres in the gel.

Other suitable materials for the scaffold fibrils or fibres of the gel casting material may include synthetic polymers i.e. polymers that are not naturally present in the human or animal body. Suitable polymers include organic polymers such as polylactones (e.g. PLA, PGA and PCL), polyethylene glycol (PEG), inorganic polymers such as phosphate glass and synthetic, gelling polypeptide gels. Alternatively or additionally other fibre-like or fibre-forming materials could be used, e.g carbon nanotubes.

In some embodiments, the gel may comprise two or more different types of fibril or fibre. For example, the scaffold may comprise: fibronectin and collagen; collagen and polylactide; collagen and albumin; fibrin and collagen; collagen and carbon-nanotubes; fibrinogen and collagen; fibrinogen, collagen and fibronectin or fibrin, collagen and fibronectin. The interstitial fluid phase of the gel casting material may comprise an aqueous liquid. For example, the fluid phase may be water with solutes such as salts and proteins dissolved therein. Alternatively the interstitial fluid phase may comprise an alcohol. In some embodiments, the fluid phase may be a cell culture medium suitable for the growth and proliferation of cells. The interstitial fluid phase may contain cells or groups of cells (e.g. co-cultures, spheroids, organoids).

The gel casting material may further comprise one or more cross-linking agents, e.g. enzymatic or chemical cross-linking agents. For example, the gel casting material may comprise one or more of biocompatible transglutaminase, glutaraldehyde, EDC/NHS, genipin, proanthocyanidin, lysyl Oxidase, and/or lysyl oxidase homolog 2. Genipin or transglutaminase may be particularly advantageous as they have been reported to have minimal cytotoxic effects on biological tissue. Lysyl oxidase, and/or lysyl oxidase homolog 2 may also be advantageous, as these crosslinking agents may produce crosslinks similar to that found in native tissue, in particular when used for crosslinking of collagen. The crosslinking agent may be carried in a suitable solvent, for example water or ethanol.

In some embodiments, the tissue equivalent tubular scaffold may be cross-linked after densification. In this way it may be possible to provide for controlled cross-linking of the tissue equivalent tubular scaffold. For example, the tissue equivalent tubular scaffold may be disposed in a bath containing a suitable cross-linking agent (for example, an enzymatic or chemical crosslinking agent). Alternatively, a physical cross-linking step may be performed on the tissue equivalent tubular scaffold (e.g. by UV irradiation, or by dehydrothermal (DHT) treatment). UV irradiation is a quick and highly controllable way of crosslinking some materials, for example collagen. DHT treatment is performed by applying a vacuum and raising the temperature of the scaffold to 110° C.

Such cross-linking agents can provide crosslinking (enzymatically, thermally or otherwise) of the scaffold during after densification, which can improve the mechanical properties of the resulting scaffold (e.g. strength, Young's modulus).

In preferred embodiments, the gel casting material comprises a collagen hydrogel, the collagen hydrogel optionally comprising one or more additional scaffold fibril or fibre materials. The collagen hydrogel may have a collagen concentration of from 1 mg/ml to 10 mg/ml, more preferably 2.5 to 7.5 mg/ml, most preferably about 5 mg/ml.

The hydrophilicity and/or the pore size of the porous end part of the elongate mould portion of the casting chamber may be selected so as to determine the rate at which the fluid phase of the gel casting material can flow from the elongate mould portion. The porous end part of the elongate mould portion may be formed from one or both of a hydrophilic material and/or a hydrophobic material. The average pore size of the porous end part of the elongate mould portion may be from 0.025 µm to 10 µm, preferably from 0.2 µm to 5 µm, more preferably from 1.2 to 5 µm. The pore size of the porous end part may be selected based on the concentration of the gel casting material (i.e. proportion of solid phase) and may also be selected based on densification temperature. When the porous end part has an average pore size of smaller than 0.025 µm, this may undesirably restrict fluid flow out of the elongate mould portion. When the porous end part has an average pore size of larger than 5 µm, this may cause rapid removal of the fluid phase of the gel casting material, leading to poor densification.

In some arrangements, the porous end part of the elongate mould portion may be an end face of the elongate mould portion. The porous end part of the elongate mould portion may be provided by a porous member disposed to close an end of the elongate mould portion. The porous member may comprise one or more porous membranes. For example, two or more membranes may be used in combination. Stacking two or more membranes may reduce the effective pore size and slow the rate of fluid removal from the elongate mould portion. One particularly preferred arrangement is a combination of two 1.2 µm-pore-size membranes. In some cases, it may be advantageous to use a combination of both a hydrophilic and a hydrophobic membrane, in particular, where the pore size of one or more of the membranes is larger than the size of the scaffold fibres or fibrils. In this way, initial fluid loss may be prevented, in particular for embodiments where gelation of the gel casting material occurs in-situ, due to the presence of the hydrophobic membrane. The hydrophobic membrane can then be removed before allowing axial flow of the fluid phase of the gel casting material out of the porous end part of the elongate mould portion provided by the remaining hydrophilic membrane to thereby provide rapid densification of the gel casting material.

Examples of suitable materials for the porous end part of the elongate mould portion include e.g. nylon woven net filter (hydrophilic) with 5 µm pores, nylon membrane filters (hydrophilic) with 0.2 µm pores, mixed cellulose ester membrane filters (hydrophilic) with 0.025 µm pores. Examples of hydrophobic membranes include a Mitex™ PTFE membrane (hydrophobic) with 5 µm pores. However a wide range of other materials may be suitable. Some further suitable materials include but are not limited to: hydrophilic polycarbonate membranes, PVDF hydrophilic membranes, PES hydrophilic membranes, and hydrophilic PTFE membranes.

The step of allowing axial flow of the fluid phase of the gel casting material out of the elongate mould portion, for example via an outlet or via a porous end part of the elongate mould portion may be performed by any suitable method. For example, in one arrangement, axial flow may occur under gravity due to the hydrostatic pressure of the gel casting material within the casting chamber.

The method may include a step of contacting the outlet or porous end part of the elongate mould portion with an absorbent medium to cause flow of the fluid phase of the casting material out of the elongate mould portion. The absorbent medium may comprise any material which can absorb the fluid phase of the gel casting material. Conveniently, the absorbent medium may comprise one or more paper towels, however the skilled person is well aware of a wide range of suitable alternative absorbent materials. The volume of the absorbent medium provided (for example, the number of paper towels) may be selected based on the amount of fluid to be removed from the casting chamber. The absorbent medium may be heated to promote evaporation of the absorbed fluid phase from the absorbent medium. Alternatively or additionally, the method according to the present invention may be performed in a low-humidity environment. This may help to prevent saturation of the absorbent medium, which can greatly slow the densification process.

Alternatively or additionally, axial flow of the fluid phase of the gel casting material may be provided by application of a vacuum to the outlet or porous end part of the elongate mould portion. The casting chamber may further comprise a reservoir portion which is fluidly connected to the elongate mould portion. The reservoir portion may be fluidly connected to the elongate mould portion by a curved transition section between the reservoir portion and the elongate mould portion. In other words, the interior surface of the casting chamber may be curved at a boundary between the reservoir portion and the elongate mould portion. This may allow for more homogeneous densification of the casting material, by preventing coalescence of fibrils or fibres at the boundary between the reservoir portion and the elongate mould portion of the casting chamber.

Preferably, during use, the reservoir portion of the casting chamber is disposed vertically above the elongate mould portion. In this way, gel casting material contained in the reservoir portion can flow into the elongate mould portion as gel casting material within the elongate mould portion densifies (and accordingly reduces in volume).

The shape of the reservoir portion is not particularly limited, but in some arrangements, the reservoir may be funnel-shaped, for example, being or comprising a conical funnel being formed at an angle of between 2.5° and 80° relative to the longitudinal axis of the cone. In some arrangements, the funnel-shape reservoir has an upwardly extending straight-walled cylindrical portion connected to a conical funnel portion. It is hypothesised that extending the funnel-shaped reservoir in such a manner may lead to an improvement in the uniformity of the densified gel casting material along the length of the resulting tissue equivalent tubular scaffold.

It can be considered that the casting material is deformed during densification from a first shape (the shape of the reservoir portion) to a second shape (the shape of the elongate mould portion). For example, where the reservoir portion is funnel shaped, and the elongate mould portion is cylindrical, the casting material undergoes a cone-to cylinder deformation during densification.

Typically, the volume of the reservoir portion will be larger than the volume of the elongate mould portion. Provision of a reservoir portion can allow a larger volume of gel casting material to be densified within the elongate mould portion. The total internal volume of the casting chamber may be e.g. 10 ml or more, for example 15 ml or more, 20 ml or more, 50 ml or more or 100 ml or more. The maximum total internal volume of the casting chamber is not particularly limited. The total internal volume of the casting chamber may be selected based on the desired volume of the resultant tubular scaffold.

The casting chamber may be formed from any suitable material. For example, the casting chamber may be formed from e.g. a metal (e.g. stainless steel, anodised aluminium), a glass, a biological polymer (e.g. gelatin) and/or a synthetic polymer (e.g. nylon, acrylic), or any combination of these materials. Polymeric materials may be preferred due to their low cost and ease of manufacture. The material of the casting chamber may be transparent (e.g. Perspex™ or glass). This has the advantage that the densification process can be more easily observed. Alternatively or additionally, the casting chamber may be made from a hydrophilic material (e.g. nylon), or the interior surface of the casting chamber may comprise a hydrophilic layer. By providing a hydrophilic interior surface of the casting chamber, an aqueous boundary lay may form between the casting material and the interior surface of the casting chamber, which may help to prevent the casting material from sticking to the casting chamber walls during densification.

In some arrangements, a lubricant may be applied to the interior surface of the casting chamber (for example, an oil-based lubricant such as sunflower oil) prior to the step of at least partly filling the casting chamber with the gel casting material. This may help to prevent the casting material from sticking to the casting chamber walls during densification.

In some embodiments, the casting chamber may be produced by an additive layer manufacturing process (e.g. 3D printing). In other embodiments the casting chamber may be formed by a machining or moulding process.

The interior surface of the casting chamber may be smoothed before use in the method according to the present invention. For example, where the casting chamber is produced by an additive layer manufacturing process, the layer-by-layer nature of such a process may leave grooves in the casting chamber which may be undesirable, and which may be removed in a smoothing step (e.g. machining, polishing, or chemical treatments, to remove said grooves). Alternatively, the casting chamber may be produced in a manner (e.g. moulding or machining) which provides substantially smooth interior walls. The lumen template is preferably centrally disposed within the elongate mould portion. Furthermore, the lumen template is preferably disposed to be substantially perpendicular to the porous end part of the elongate mould portion. In this way, a symmetrical scaffold can be formed.

The lumen template may be positioned in the elongate mould portion by fitting it to a supporting base piece which may be attached to the casting chamber beneath the porous end part of the elongate mould portion. Such an arrangement may require a hole to be provided in the porous end part of the elongate mould portion, to allow the lumen template to pass through. In some arrangements, an attachment member may be provided on the supporting base piece (for example a screw), by which the lumen template can be attached to the supporting base piece. In such an arrangement, the screw may pass through the porous end part of the elongate mould portion (for example, by means of a hole formed in the porous end part of the elongate mould portion).

In a preferred embodiment, the lumen template may be disposed within the elongate mould portion by mounting from above the casting chamber. For example, the lumen template may be held by a supporting lid piece. In such an arrangement, the lumen template preferably extends through the entire casting camber to contact the porous end part of the elongate portion of the casting chamber.

The lumen template and/or one or more walls of the elongate mould portion may be provided with a patterned surface. The patterned surface may comprise a plurality of surface features comprising e.g. ridges, grooves, recesses and/or projections (e.g. pillars). The surface features may be selected to replicate native tissue structures. The surface features may project or be recessed approximately 250 μm to 2 mm above or below the surface on which they are formed. The size of such surface features may alternatively be selected to be a predetermined proportion of the lumen diameter. For example, the surface features may project or be recessed a distance less than or equal to 50% of the lumen diameter, less than or equal to 40% of the lumen diameter, less than or equal to 30% of the lumen diameter, less than or equal to 20% of the lumen diameter, less than or equal to 10% of the lumen diameter or less than or equal to 5% of the lumen diameter. During casting, the gel casting material will infiltrate the surface features of the lumen template and/or elongate mould portion, and these features will be reproduced in the resultant tubular scaffold. For example, the lumen template may be provided with a plurality of recesses (pillar-shaped recesses about 500 μm deep, with a cross-section of about 250 μm×250 μm may be particularly suitable): this will result in a scaffold comprising a plurality of luminal projections, which may mimic villi on the luminal surface of the small intestine.

The patterned surface may be provided by machining or otherwise shaping the surface of the lumen template and/or the elongate mould portion. Alternatively, the patterned surface may be provided by forming a patterning layer on the lumen template and/or one or more walls of the casting chamber. Such a patterning layer may be formed by casting a patterning material around or onto the lumen template and/or the elongate mould portion using a patterning mould, which may be formed by e.g. 3D printing or laser-assisted methods. The patterning mould may be dissolvable in a suitable solvent. This can enable a wide range of surface features to be fabricated.

The patterning material may be a material which can be selectively removed after densification of the gel casting material without damaging the tubular scaffold. Selective removal may be performed by selectively degrading the patterning material, or by otherwise changing the physical state of the patterning material. For example, the patterning material may be selected to have a melting and/or gelation temperature which is different to a melting temperature and/or a degradation temperature of the gel casting material. In this way, the patterning layer can easily be removed from the final scaffold structure by a step of heating or cooling (as appropriate) one or more of the casting chamber, the lumen template and/or the tissue equivalent tubular scaffold to melt or otherwise liquefy and remove the patterning layer. Alternatively or additionally, the patterning material may be selectively dissolvable in a suitable solvent, in which the gel casting material is not soluble. In this way, by immersing the tubular scaffold in said solvent, the patterning layer can easily be removed without damaging the tubular scaffold. Suitable patterning materials include e.g. gelatin, alginate, and methylcellulose. In one example, a calcium alginate gel could be used as the patterning material. The resulting calcium alginate patterning layer could be removed by first chelating calcium ions away with sodium citrate buffer, followed by diffusing away sodium alginate. In another example, methylcellulose gel could be used as the patterning material. Methylcellulose gel is a reverse thermo-gelling hydrogel which is liquid at low temperature, and a gel at high temperature. The resulting patterning layer could then be removed by cooling of one or more of the casting chamber, the lumen template and/or the tissue equivalent tubular scaffold to below the gel temperature of methylcellulose to thereby liquefy and remove the methyl cellulose patterning layer. In another example, the gelatin gel could be used as the patterning material. The resulting patterning layer could then be removed by heating of one or more of the casting chamber, the lumen template and/or the tissue equivalent tubular scaffold to above the melting temperature of the gelatin to thereby melt and remove the patterning layer.

The method may include a further step of seeding the tissue equivalent tubular scaffold with cells. A wide range of methods for seeding scaffolds with cells are well known to the skilled person. However, in one embodiment, a suspension of cells in cell medium is introduced to a lumen of the scaffold. Optionally, the scaffold is rotated during or after introduction of the cell suspension to the scaffold. This may allow for more even seeding of cells across the scaffold.

Alternatively or additionally, the method may include a step of encapsulating cells within the gel casting material prior to densification of the casting material. This may allow for more complex tissue types to be produced, for example, allowing for potential micro-vasculature network formation. This can be supported by the addition of proteins (e.g. extracellular matrix proteins, such as fibronectin, laminin) and growth factors (e.g. VEGF, bFGF). Densification of the casting material will lead to resulting densification of supporting proteins and growth factors which may have beneficial effects on the cell response.

For example, cells may be mixed into a gel casting material precursor solution, which is subsequently gelled to thereby encapsulate the cells within the gel casting material. During densification of the gel casting material, the cells remain encapsulated within the casting material and are thereby included in the resulting tissue equivalent tubular scaffold. Preferably, where cells are encapsulated within the gel casting material, densification is performed under incubation conditions (e.g. 37° C., 5% $CO_2$), although this is not essential, and it may be adequate to maintain the cells at e.g. room temperature whilst densification occurs. Since the densification process reduces the volume of the gel casting material significantly, the cell density, as well as the concentration of further components of the gel casting material (e.g. growth factor, cytokine concentration etc.) can be substantially increased in the resulting tubular scaffold as compared with the gel casting material comprising the encapsulated cells.

Cells seeded on the tissue equivalent tubular scaffold, or encapsulated within the gel casting material may be cells that confer tissue functionality and provide structures which replace or facilitate the repair of endogenous tissue. For example, such cells may comprise one or more of: muscle cells to provide contractile structures, vascular and/or neural cells to provide conductive elements, metabolically active secretory cells, such as liver cells, hormone synthesising cells, sebaceous cells, pancreatic islet cells or adrenal cortex cells to provide secretory structures, stem cells, such as bone marrow-derived or embryonic stem cells, dermal fibroblasts, skin keratinocytes, (and combination layers of the two), Schwann cells for nerve implants, intestinal epithelial and stem cells, colonic epithelial and stem cells, lung epithelial and stem cells, immune system cells, smooth muscle cells, pericytes, mesenchymal stem cells, endothelial cells (for example HUVECs), urothelial and smooth muscle cells for bladder/urethra structures; cholangiocytes and other biliary cells for biliary structures; osteoblasts, osteoclasts and osteocytes for bone structures; oesophageal and tracheal cells for respiratory structures; tenocytes for tendon structures; and chondrocytes for cartilage structures.

Cells seeded on the tissue equivalent tubular scaffold, or encapsulated within the gel casting material may include primary cells, for example cells obtained from a tissue that confer functionality of the tissue onto the scaffold.

Cells seeded on the tissue equivalent tubular scaffold, or encapsulated within the gel casting material may also include cell lines and cells differentiated or otherwise obtained from induced pluripotent stem cells (iPSCs).

Cells seeded on the tissue equivalent tubular scaffold, or encapsulated within the gel casting material may be provided as single cells, spheroids and/or organoids. Organoids may have an advantage over single cells in terms of survivability and functionality, and can produce larger vessel hierarchies than simple co-culture systems.

Combination layers of cells may be provided. Preferably such combination layers may comprise concentric layers. For example, a first layer of a first type of cell (e.g. smooth muscle cells or pericytes) may be seeded on the tubular scaffold, and a second layer of a second type of cell (e.g. epithelial cells) may be subsequently seeded on the tubular scaffold, thereby creating concentric layers of cells.

Additionally or alternatively, combination layers may be provided in an axial direction, to thereby form a tube having a plurality of distinct cell domains in an axial direction. This may be achieved by e.g. providing first and second gel casting material precursor solutions respectively comprising first and second kinds of cell, sequentially casting and gelling the first and second precursor solutions within the casting chamber before densifying the gel casting material within the elongate mould portion to form a tissue equivalent tubular scaffold having two distinct cell domains in an axial direction.

In some arrangements, complex combination layers may be provided. The geometry of complex combination layers may vary along the length of the tissue equivalent tubular scaffold. For example, certain regions near the interface of two different primarily axial domains may also have two distinct cell domains in the radial direction as well (e.g. one cell type wrapped around the lumen). This effect may occur as a result of casting chamber geometry, due to the mapping of one volume shape (funnel) to another (cylinder) during densification.

The method may further comprise a step of covering the casting chamber to substantially prevent evaporation from within the casting chamber, after the step of at least partly filling the casting chamber, and before the step of allowing axial flow of the fluid phase of the casting material out of the casting chamber. For example, a lid piece may be provided which extends across an open end of the casting chamber. Optionally, the lid piece may comprise a through-hole to allow for pressure equalisation between the casting chamber and the atmosphere. Such a through-hole may be covered with a plastic film (e.g. Parafilm™) when appropriate. Alternatively, an open end of the casting chamber may be covered with plastic film e.g. Parafilm™. By substantially preventing evaporation from within the casting chamber, it may be possible to reduce or prevent radial densification of the scaffold structure. Furthermore, this may prevent formation of a densified region forming at the top surface of the casting material which can inhibit optimal densification.

After the gel casting material has been densified within the elongate mould portion to form the tissue equivalent tubular scaffold, it may be removed from the casting chamber for use. The method may further comprise an optional evaporative drying step after removal of the tissue equivalent tubular scaffold from the casting chamber. For example, the tissue equivalent tubular scaffold can be extracted from the casting chamber still mounted on the lumen template, or an extracted tissue equivalent tubular scaffold can be re-mounted on a lumen template, and can be further densified radially inwards through evaporation, for example by leaving it suspended in a biological cabinet for a specified period of time, e.g. between 1 hour and 48 hours, although preferably no more than 4 hours for a cell-seeded scaffold. The time required for evaporative densification may depend on environmental conditions (humidity, temperature, air flow, etc.) and on the initial concentration of the gel casting material. Performing an additional evaporative drying step may enable the formation of fine tissue equivalent tubular scaffolds, e.g. for use as nerve conduits. By performing an additional evaporative drying step, the tube wall thicknesses can be reduced by a significant amount, for example up to an order of magnitude. It has been found that the reduction in the wall thickness is dependent upon the initial concentration of the gel casting material—e.g. for a densified collagen tube with 2.5 mm wall thickness and a 1 mg/mL starting collagen concentration, it may be possible to reduce wall thickness to down to 250 µm by evaporative drying. For a densified collagen tube with 2.5 mm wall thickness and a 2.5 mg/mL starting collagen concentration, it may be possible to reduce wall thickness to down to 500 µm by evaporative drying. For a densified collagen tube with 2.5 mm wall thickness and a 5 mg/mL starting collagen concentration, it may be possible to reduce wall thickness to down to 1 mm by evaporative drying.

In a second aspect, the present invention provides a tissue equivalent tubular scaffold produced according to the first aspect. Various features of scaffolds produced according to the first aspect are set out above. Such scaffolds have a novel structure resulting from the mode of densification of the scaffold structure. In particular, scaffolds produced according to the present invention may comprise a seamless tubular network of scaffold fibres. Additionally, the scaffold fibre alignment may be different in scaffolds produced according to the present invention as compared with prior art scaffolds.

The tubular scaffold may comprise a tube wall surrounding an internal lumen. The tube wall may be substantially cylindrical. Preferably the tubular scaffold is human-sized. The tubular scaffold may have an average outer diameter of from about 2 mm to about 40 mm. For example, the average outer dimeter of the tubular scaffold may be 2 mm or more, 3 mm or more, 4 mm or more, 5 mm or more, 10 mm or more or 20 mm or more. The average outer diameter of the tubular scaffold may be 40 mm or less, 30 mm or less or 20 mm or less.

The tubular scaffold may have an average lumen diameter of about 0.01 mm to about 20 mm. For example, the average lumen diameter may be 0.01 mm or more, 0.1 mm or more, 0.5 mm or more, 1 mm or more, 5 mm or more, or 10 mm or more. The average lumen diameter may be 20 mm or less or 10 mm or less.

The resulting tubular scaffold may have an average tube wall thickness of from about 0.5 mm to about 20 mm, preferably about 1 mm to 10 mm, although the inventors suggest that there is potentially no upper limit to the possible wall thicknesses which it is possible to produce according to the method of the invention.

As discussed above, the length of the tubular scaffold is not particularly limited. The preferred length depends on the application for which the scaffold is intended. For example, whilst tubular scaffolds for use in biliary research may require a length of only around 15 mm, tubular scaffolds for use in e.g. intestinal research may require a length of e.g. 1 m or more. Typical lengths suitable for use in a range of applications may be from e.g. 1 cm and 30 cm. For example, the tubes may have a length of about 2 cm, about 3 cm, about 4 cm, about 5 cm, about 10 cm, about 15 cm, about 20 cm, about 25 cm or about 30 cm.

The tubular scaffold may have a uniform density along the length of the scaffold. Alternatively, the tubular scaffold may have a density gradient along the length of the scaffold. A density gradient here refers to a gradient in fibril density.

Scaffolds produced according to the present invention may find particular use in transplantation as a replacement for damages or diseased tissues and organs in humans or otherwise. In particular, human-sized scaffold structures, such as densified collagen tubes, are bioactive, biocompatible, reproducible, customizable (inner and outer diameter, wall thickness), biodegradable, mechanically comparable to native tissue, and cells can be encapsulated into the walls of the tube or seeded upon the surfaces. Upon seeding with cells, scaffolds produced as described herein are applicable to a wide range of human diseases that require surgical replacement of tissue structures.

For example, one potential application of the tissue equivalent tubular scaffolds described herein is use in vascular tissue engineering, for example in provision of an alternative to native veins and arteries for vascular surgery, i.e. a vascular scaffold. Another potential application is use in biliary tissue engineering, for example in provision of replacements for biliary tissues such as a bile duct. Another potential application includes the creation of arterio-venous (AV) shunts for renal replacement therapy. Another potential application is in production of grafts for transplantation to patients having short bowel syndrome [30], bowel cancer, diverticular disease, inflammatory bowel diseases (such as Crohn's disease or ulcerative colitis), and/or intestinal failure, i.e. an intestinal scaffold or colonic scaffold. Here, the tubular scaffold may be seeded with intestinal stem cells and/or intestinal organoids. Additionally, tubular scaffolds having a patterned luminal surface may be advantageous in such applications as they may more closely resemble the crypt-villus architecture of the intestine. Another potential application is in tracheal tissue engineering. The method disclosed herein allows tubular scaffolds to be fabricated with large diameters, thick-walled structures, and branching arrangements. Accordingly they may be suitable for provision of replacements for diseased tracheal, bronchial and oesophageal tissues, i.e. as a tracheal scaffold, a bronchial scaffold and/or an oesophageal scaffold. Further applications include use as a neural scaffold, a fallopian tube scaffold, a ureteral scaffold, and/or as a urethral scaffold.

For use as a bile duct scaffold, the tissue equivalent tubular scaffold may have a luminal diameter of from 1.5 to 10.9 mm, preferably about 4 mm. The tissue equivalent tubular scaffold may have a wall thickness of from 1 to 1.5 mm. The tissue equivalent tubular scaffold may be populated with one or more cells (single cells, spheroids or organoids) selected from: cholangiocytes (biliary epithelial cells), biliary fibroblasts, vascular (endothelial) cells, immune cells, pluripotent stem cells, mesenchymal stem cells, other liver-related cell types (e.g. intrahepatic biliary tissue, Kupffer cells, etc).

For use as an arterial scaffold, for example, a cardiac coronary artery (left main) scaffold, the tissue equivalent tubular scaffold may have a luminal diameter of from 4 to 5 mm, preferably about 4.5 mm. The tissue equivalent tubular scaffold may have a wall thickness of from 0.55 to 1.0 mm, preferably about 1 mm. The tissue equivalent tubular scaffold may be populated with one or more cells (single cells, spheroids or organoids) selected from: Coronary artery endothelial cells, smooth muscle cells, vascular (endothelial) cells, immune cells, pluripotent stem cells, mesenchymal stem cells.

For use as a vascular scaffold, the tissue equivalent tubular scaffold may have an outer diameter of from 5 to 30 mm. The tissue equivalent tubular scaffold may have a wall thickness of from 1 to 5 mm. The tissue equivalent tubular scaffold may be populated with one or more cells (single cells, spheroids or organoids) selected from: Vascular endothelial cells, smooth muscle cells, immune cells, pluripotent stem cells, mesenchymal stem cells.

For use as a ureteral scaffold the tissue equivalent tubular scaffold may have a luminal diameter of from 1.5 to 8 mm, preferably about 3 mm. The tissue equivalent tubular scaffold may have a wall thickness of from 1 to 1.5 mm. The tissue equivalent tubular scaffold may be populated with one or more cells (single cells, spheroids or organoids) selected from: Urothelial (epithelial) cells, smooth muscle cells, urinary bladder fibroblasts, vascular (endothelial) cells, immune cells, pluripotent stem cells, mesenchymal stem cells.

For use as a urethral scaffold the tissue equivalent tubular scaffold may have an outer diameter of from 5 to 8 mm, preferably about 6 mm. The tissue equivalent tubular scaffold may have a wall thickness of from 1 to 1.5 mm. The tissue equivalent tubular scaffold may be populated with one or more cells (single cells, spheroids or organoids) selected from: Urothelial (epithelial) cells, smooth muscle cells, urinary bladder fibroblasts, vascular (endothelial) cells, immune cells, pluripotent stem cells, mesenchymal stem cells.

For use as a duodenal scaffold (intestinal scaffold) the tissue equivalent tubular scaffold may have an outer diameter of from 20 to 40 mm, preferably about 25 mm. The tissue equivalent tubular scaffold may have a wall thickness of from 1.5 to 3 mm, preferably about 1.5 mm. The tissue equivalent tubular scaffold may be populated with one or more cells (single cells, spheroids or organoids) selected from: Enterocytes (intestinal epithelial cells), secretive cell types (goblet, Paneth, enteroendocrine), vascular cells (human intestinal microvascular endothelial), immune cells, pluripotent stem cells, mesenchymal stem cells.

For use as an ileum scaffold (intestinal scaffold) the tissue equivalent tubular scaffold may have an outer diameter of from 20 to 40 mm, preferably about 20 mm. The tissue equivalent tubular scaffold may have a wall thickness of from 1.5 to 3 mm, preferably about 1.5 mm. The tissue equivalent tubular scaffold may be populated with one or more cells (single cells, spheroids or organoids) selected from: Enterocytes (intestinal epithelial cells), secretive cell types (goblet, Paneth, enteroendocrine), vascular cells (human intestinal microvascular endothelial), immune cells, pluripotent stem cells, mesenchymal stem cells.

For use as a colonic scaffold the tissue equivalent tubular scaffold may have an outer diameter of from 20 to 60 mm. The tissue equivalent tubular scaffold may have a wall thickness of from 1.5 to 3 mm, preferably about 1.5 mm. The tissue equivalent tubular scaffold may be populated with one or more cells (single cells, spheroids or organoids) selected from: Enterocytes (intestinal epithelial cells), secretive cell types (goblet, Paneth, enteroendocrine), vascular cells (human intestinal microvascular endothelial), immune cells, pluripotent stem cells, mesenchymal stem cells.

For use as a neural scaffold, for example, as a peripheral nerve scaffold, the tissue equivalent tubular scaffold may have a diameter of from 20 µm to 0.6 mm, for example 20 to 60 µm (for use as a retinal nerve fibre bundle), or from 0.4-0.6 mm (for use as an arm nerve fascicule). The tissue equivalent tubular scaffold may be populated with one or more cells (single cells, spheroids or organoids) selected from: Ganglion cell axons, neurons, glial cells, vascular (endothelial) cells, immune cells, pluripotent stem cells, mesenchymal stem cells.

For use as an oesophageal scaffold the tissue equivalent tubular scaffold may have a luminal diameter of from 15 to 30 mm. The tissue equivalent tubular scaffold may have a wall thickness of from 3 to 8 mm, preferably about 5 mm. The tissue equivalent tubular scaffold may be populated with one or more cells (single cells, spheroids or organoids) selected from: Squamous epithelial cells, dysplastic columnar cells (disease modelling), vascular (endothelial) cells, smooth muscle cells, immune cells, pluripotent stem cells, mesenchymal stem cells.

For use as a tracheal scaffold the tissue equivalent tubular scaffold may have a luminal diameter of from 15 to 30 mm. The tissue equivalent tubular scaffold may have a wall thickness of from 3 to 8 mm, preferably about 5 mm. The tissue equivalent tubular scaffold may be populated with one or more cells (single cells, spheroids or organoids) selected from: Tracheal epithelial cells (basal, goblet, and ciliated cells), vascular (endothelial) cells, smooth muscle cells, immune cells, pluripotent stem cells, mesenchymal stem cells.

For use as a fallopian tube scaffold the tissue equivalent tubular scaffold may have a luminal diameter of from 2.5 to 6 mm. The tissue equivalent tubular scaffold may have a wall thickness of from 2 to 3 mm.

The tissue equivalent tubular scaffold may be populated with one or more cells (single cells, spheroids or organoids) selected from: Columnar ciliated epithelial cells, secretory cells, narrow peg cells, vascular (endothelial) cells, smooth muscle cells, immune cells, pluripotent stem cells, mesenchymal stem cells. The exemplary sizes given above for use in specific applications are based on typical dimensions for healthy, human adults. However, in some cases it may be advantageous to use a scaffold of a slightly different size. For example, the dimensions of equivalent tissues in children may be smaller than the dimensions given above, and accordingly it may be advantageous to produce tissue equivalent tubular scaffolds with dimensions smaller than listed above. Conversely, diseased conduits may distend, therefore resulting in tissues having larger dimensions that those listed above. Accordingly it may be advantageous to produce tissue equivalent tubular scaffolds having dimensions larger than listed above, in particular for use in disease model applications.

The tissue equivalent tubular scaffold is preferably fixable at a site of tissue damage. For example, the scaffold may be fixable such that a first end of the scaffold is located adjacent the proximal stump of a damaged tissue and a second end is located adjacent the distal stump of a damaged tissue. The tissue equivalent implant may be fixed by any convenient technique. For example, it may be sutured or glued in place.

Another aspect of the invention provides a method of treatment of a damaged tissue in an individual comprising fixing a tissue equivalent tubular scaffold produced using a method described herein to said damaged tissue to repair and/or replace said tissue.

Related aspects provide a tissue equivalent tubular scaffold produced using a method described herein for use in a method of treatment of a damaged tissue in an individual and the use of a tissue equivalent tubular scaffold produced using a method described herein in the manufacture of a medicament for use in a method of treatment of a damaged tissue in an individual.

Tissues suitable for treatment with a tissue equivalent tubular scaffold as described herein may include, tissues with tubular structures, for example vascular tissue, such as blood vessels; biliary tissue such as bile ducts; gastrointestinal tissue, such as oesophagus, colon, small intestine or large intestine; respiratory tissue, such as trachea and bronchi; and urinary tissue, such as ureter or urethra.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope of the present invention.

All documents and sequence database entries mentioned in this specification are incorporated herein by reference in their entirety for all purposes.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

BRIEF DESCRIPTION OF THE FIGURES

Embodiments and experiments illustrating the principles of the invention will now be discussed with reference to the accompanying figures in which.

DETAILED DESCRIPTION

In the detailed description below, various terms are used to describe to describe tissue equivalent tubular scaffolds according to the present invention. Terms such as "densified collagen tubes", "tubular scaffolds", "tubes", "collagen tubes", "densified collagen tubular scaffolds" and the like, describe tissue equivalent tubular scaffolds according to various embodiments of the present invention unless expressly indicated otherwise.

Figure 1:
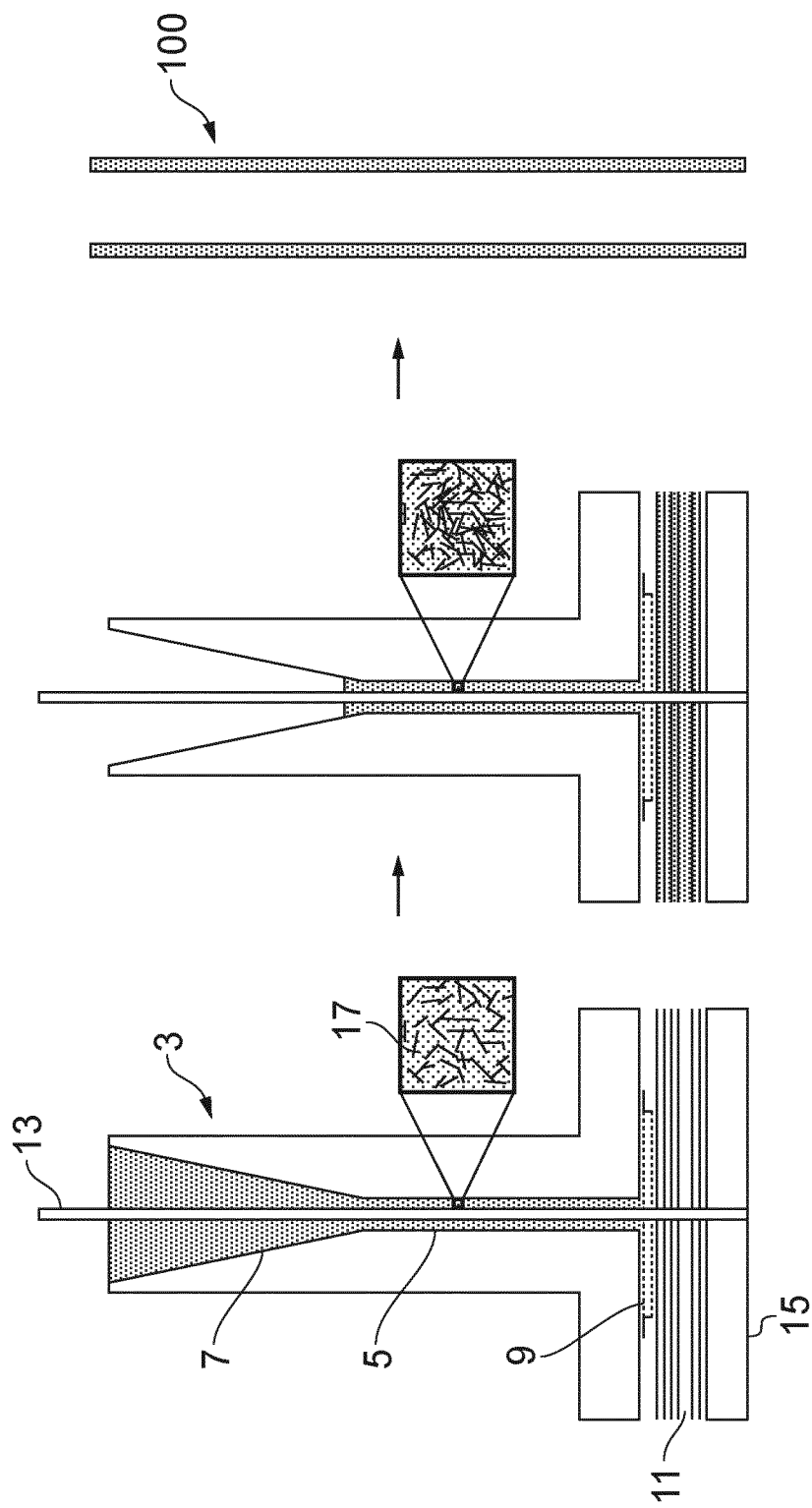
FIG. 1 is a schematic diagram showing formation of a tissue equivalent tubular scaffold according to one embodiment of the invention.

A schematic diagram showing formation of a tissue equivalent tubular scaffold according to one embodiment of the invention is shown in FIG. 1. A casting chamber 3 having a cylindrical elongate mould portion 5 and a funnel-shaped reservoir portion 7 is provided. A porous membrane 9 closes the end of the elongate mould portion, thereby forming a porous end part of the casting chamber 3. The porous membrane 9 is contacted by absorbent medium 11 which is here conveniently provided by a plurality of paper towels. A lumen template 13 in the form of a rod is disposed centrally in the casting chamber, perpendicular to the porous membrane 9. Here, the lumen template is held by a supporting base piece 15, which is disposed beneath the porous membrane and the absorbent medium. The lumen template passes through a hole formed in the porous membrane and absorbent medium. The casting chamber is filled with a gel casting material 17, here a collagen hydrogel comprising collagen fibrils and water as an interstitial fluid phase, although other gel casting materials may be used. The lumen template extends above the collagen gel.

Figure 10:
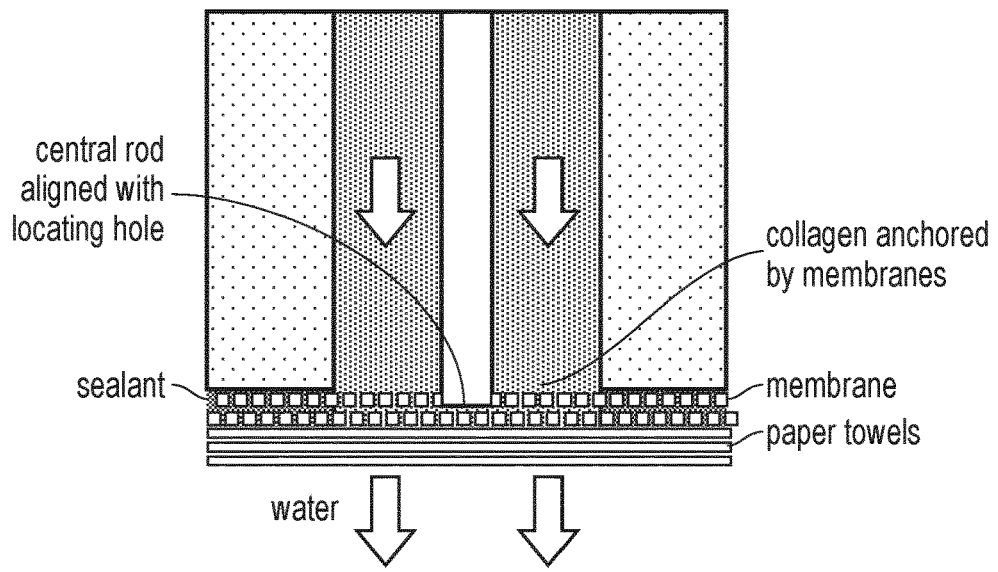
FIG. 10 is a schematic drawing showing part of an apparatus configuration for use in a method according to the invention.

An alternative arrangement for the location of the lumen template is shown in FIG. 10. Here, the lumen template ('central rod') is aligned with a locating hole formed in the membrane. A sealant is also provided to reduce leakage of the fluid phase of the gel casting material. Specifically, in this arrangement, a dental silicone was applied in a ring to the elongate mould portion of the casting chamber, and the porous membrane attached to the silicone before the completion of curing, to thereby form a strong seal between the casting chamber and the membrane (thereby providing a closed, porous end of the elongate mould portion).

As the porous membrane is contacted by the absorbent medium, water in the collagen gel flows axially out of the elongate mould portion 5 of the casting chamber 3 into the absorbent medium 11 via the porous membrane 9, whilst the collagen fibrils are retained in the casting chamber. This causes the level of casting material in the casting chamber 3 to drop as the casting material densifies within the casting chamber (show schematically in close-up). Once a desired level of densification has been achieved (i.e. some or all of the water has been removed from the casting material), the resulting tissue equivalent tubular scaffold 100, can be removed from the mould. The outer diameter of the tube is defined by the diameter of the elongate mould portion 5 of the casting chamber. The luminal diameter of the tube is defined by the outer diameter of the lumen template rod 13.

Figure 2:
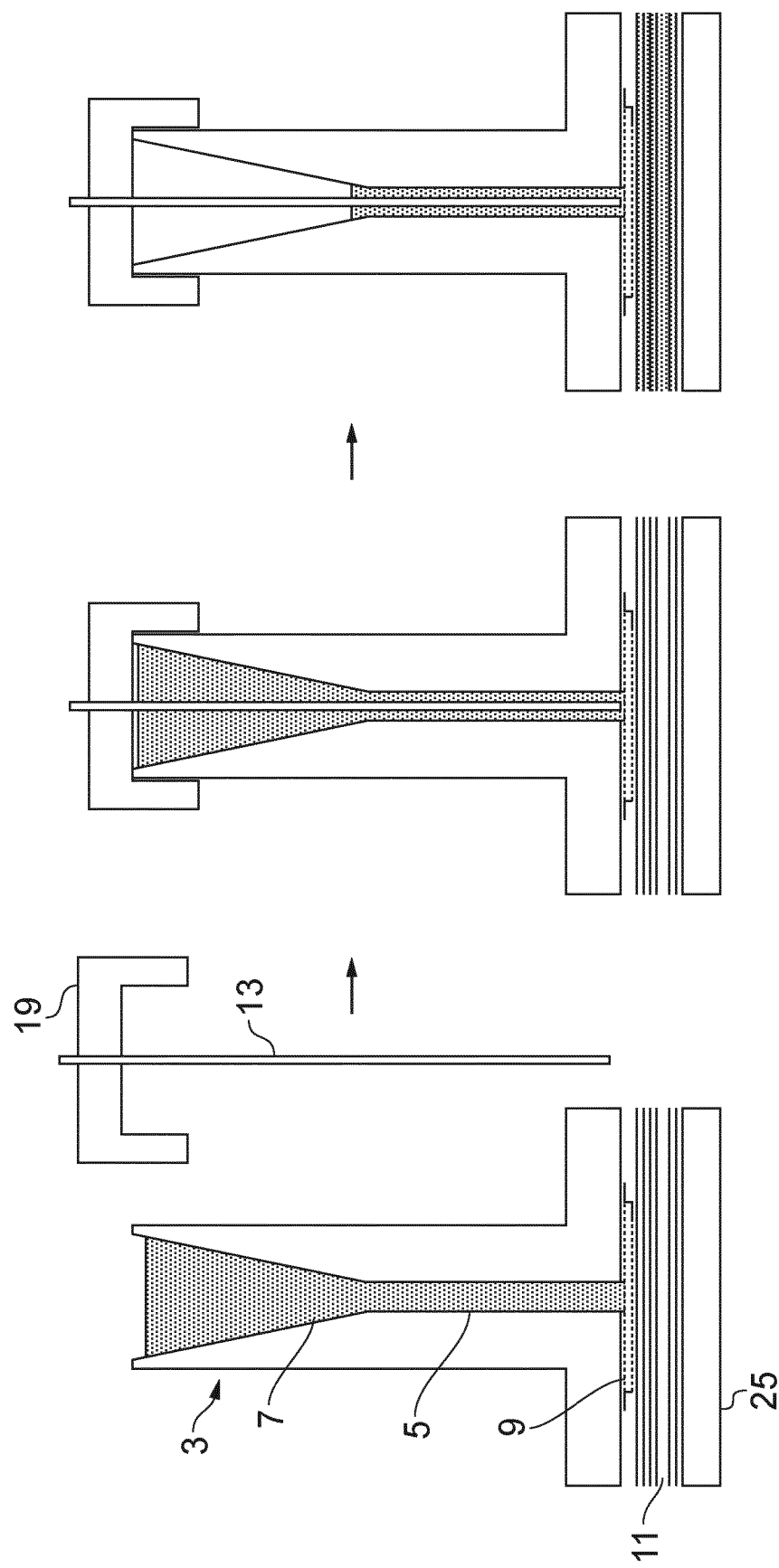
FIG. 2 is a schematic diagram showing formation of a tissue equivalent tubular scaffold according to another embodiment of the invention.

A schematic diagram showing formation of a tissue equivalent tubular scaffold according to another embodiment of the invention is shown in FIG. 2. The arrangement is generally similar to the arrangement described in FIG. 1, except that here, the lumen template 13 is not held by the base piece 25. Rather, the lumen template 13 is held by a supporting lid piece 19, configured to fit on and around the top of the casting chamber 3. The lid piece 19 has a hole formed therethrough, into which the lumen template can be fitted. The lid is then placed onto the casting chamber such that the lumen template is disposed within elongate mould portion. Here, the length of the lumen template 13 is selected such that it contacts the porous end part of the casting chamber, defined by the porous membrane 9. In this arrangement, it is not necessary to provide a hole through the porous membrane and/or absorbent medium. Such an arrangement may therefore provide reduced leaking of casting material from the casting apparatus.

Densification of casting material then proceedings in the manner described above in relation to FIG. 1.

Figure 3:
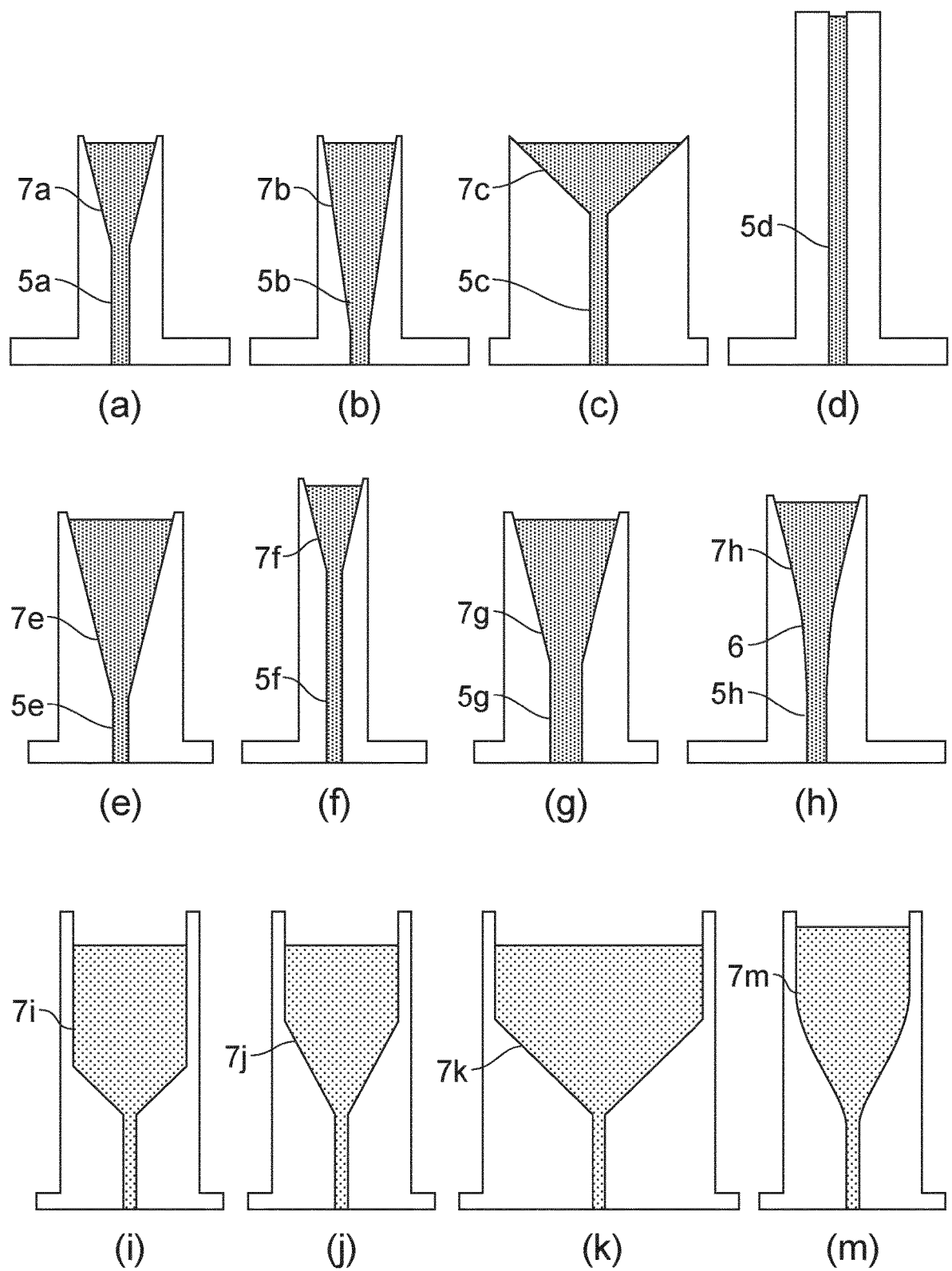
FIG. 3 is a schematic diagram showing various possible apparatus configurations suitable for use in a method according to the invention.

FIG. 3 is a schematic diagram showing various possible exemplary apparatus configurations suitable for use in a method according to the invention. As the skilled person is well aware, a wide range of alternative casting chamber shapes are possible. In these exemplary configurations, FIGS. 3(a), (b), (c), (e), (f), (g) and (h) show moulds where the casting chamber comprises a cylindrical elongate mould portion 5a,b,c,e,f,g,h and a conical-funnel-shaped upper reservoir portion 7a,b,c,e,f,g,h of varying sizes. FIGS. 3 (i), (j), (k), (m) show further configurations where the upper reservoir portion 7i,j,k,m comprises a conical-funnel-shaped section and a straight-walled cylindrical section.

In FIG. 3(a) the conical funnel is formed at an angle of about 10° relative to the longitudinal axis of the cone; in FIG. 3(b) the conical funnel is formed at an angle of about 2.5° relative to the longitudinal axis of the cone; in FIG. 3(c) the conical funnel is formed at an angle of about 45° relative to the longitudinal axis of the cone.

FIG. 3(d) shows a configuration in which the casting chamber consists only of a cylindrical elongate mould portion 5d.

The height of the funnel and height of the cylindrical elongate mould portion can varied independently of one another, and independent of the angle of the conical funnel. In FIG. 3(e) the conical funnel is lengthened while cylindrical elongate mould portion is kept short (the reservoir portion is longer than the elongate mould portion); in FIG. 3(f) the cylindrical elongate mould portion is lengthened while the conical funnel is kept short (the reservoir portion is shorter than the elongate mould portion).

In some arrangements, cylindrical elongate mould portions with large diameters may require a larger conical funnel due to an increased requirement for casting material during densification. FIG. 3(g) shows the cylindrical elongate mould portion with a large diameter and a lengthened conical funnel (with 10° angle).

FIG. 3(h) shows apparatus configuration with curved transition section 6 between the reservoir portion and the elongate mould portion. In other words, the interior surface of the casting chamber is curved at a boundary between the conical funnel and the cylindrical elongate mould portion. The configuration shown in FIG. 3(m) similarly has a curved transition section between the reservoir portion and the elongate mould portion.

Figure 11A:
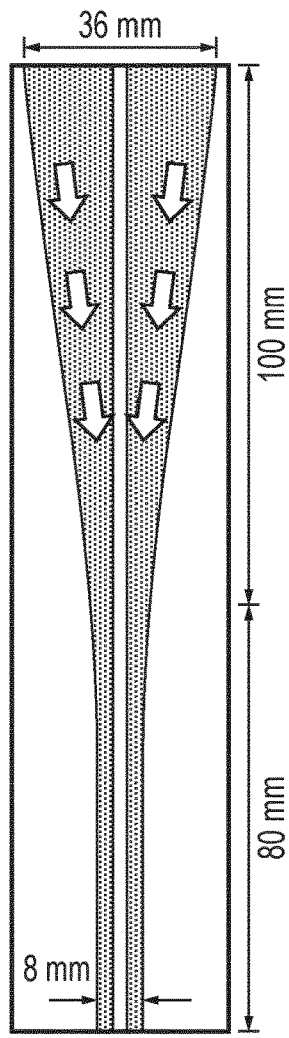
FIGS. 11(a) and (b) are schematic diagrams, each showing example casting chamber geometries.

In order to investigate the effect of different funnel geometries on the resulting tissue equivalent tubular scaffold, a study was done using two different casting chamber designs were considered, with different funnel (reservoir) shapes and identical elongate mould portions. The two different casting chamber geometries are shown in FIGS. 11(a) and (b) respectively. The casting chamber shown in FIG. 11(a) is similar in shape to that shown in FIG. 3 (h), with a curved transition section between the funnel-shaped reservoir portion and the elongate mould portion. The casting chamber shown in FIG. 11(b) is similar in shape to that shown in FIG. 3 (i).

The casting chambers were filled with a collagen gel as the gel casting material, and tissue equivalent tubular scaffold formed using a method according to the present invention. It was found that, for a given starting volume and concentration of the collagen gel precursor, the resulting tissue equivalent tubular scaffolds were different. The casting chamber shown in FIG. 11(a) (designated as Funnel A) led to formation of longer tubes with a density gradient along their length, the top part being denser than the bottom. The casting chamber shown in FIG. 11(b) (designated as Funnel B), led to tubes of uniform density, though the resulting tube was shorter than that formed using Funnel A.

Figure 11B:
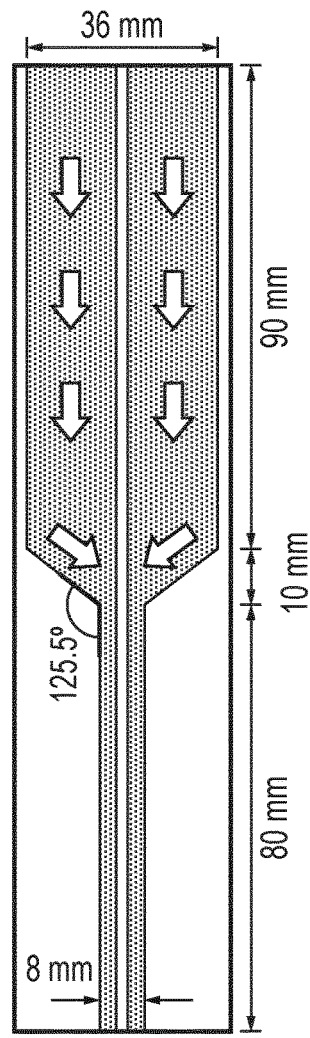
Figure 12:
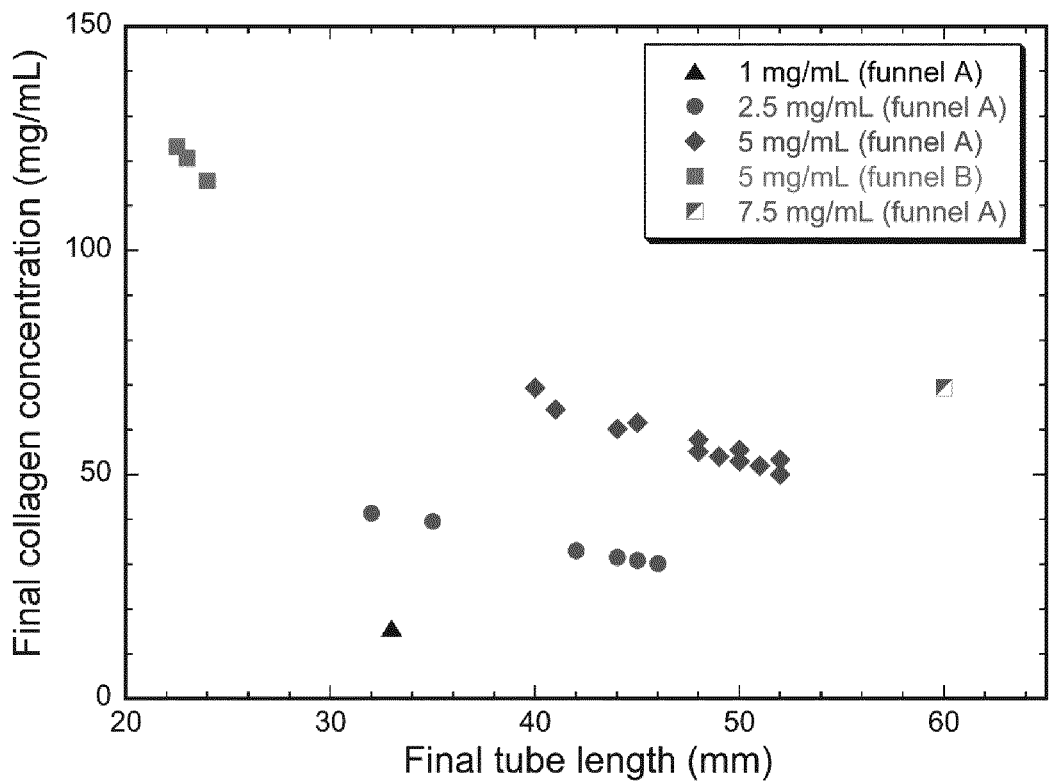
FIG. 12 is a graph showing final collagen concentration vs final tube length, for different initial collagen concentrations, for tubular scaffolds formed using the casting chambers shown in FIG. 11(a) (Funnel A) and FIG. 11(b) (Funnel B).

FIG. 12 is a graph showing final collagen concentration vs final tube length, for different initial collagen concentrations, for tubular scaffolds formed using the casting chambers shown in FIG. 11(a) (Funnel A) and FIG. 11(b) (Funnel B).

Figure 13:
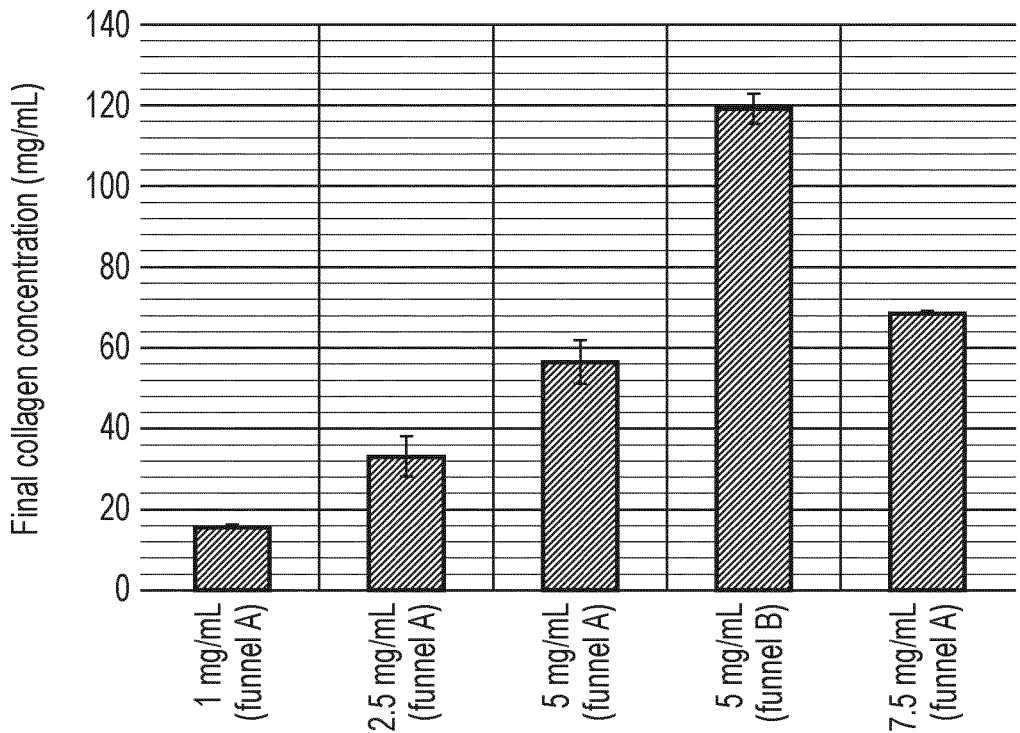
FIG. 13 is a graph showing final collagen concentrations for a range of initial collagen concentrations, for tubular scaffolds formed using the casting chambers shown in FIG. 11(a) (Funnel A) and FIG. 11(b) (Funnel B).

FIG. 13 is a graph showing final collagen concentrations for a range of initial collagen concentrations, for tubular scaffolds formed using the casting chambers shown in FIG. 11(a) (Funnel A) and FIG. 11(b) (Funnel B).

From these results, it can be seen that the final collagen concentration and the final length of the densified collagen tubes is dependent upon the starting concentration of collagen and the choice of casting chamber geometry.

Figure 4:
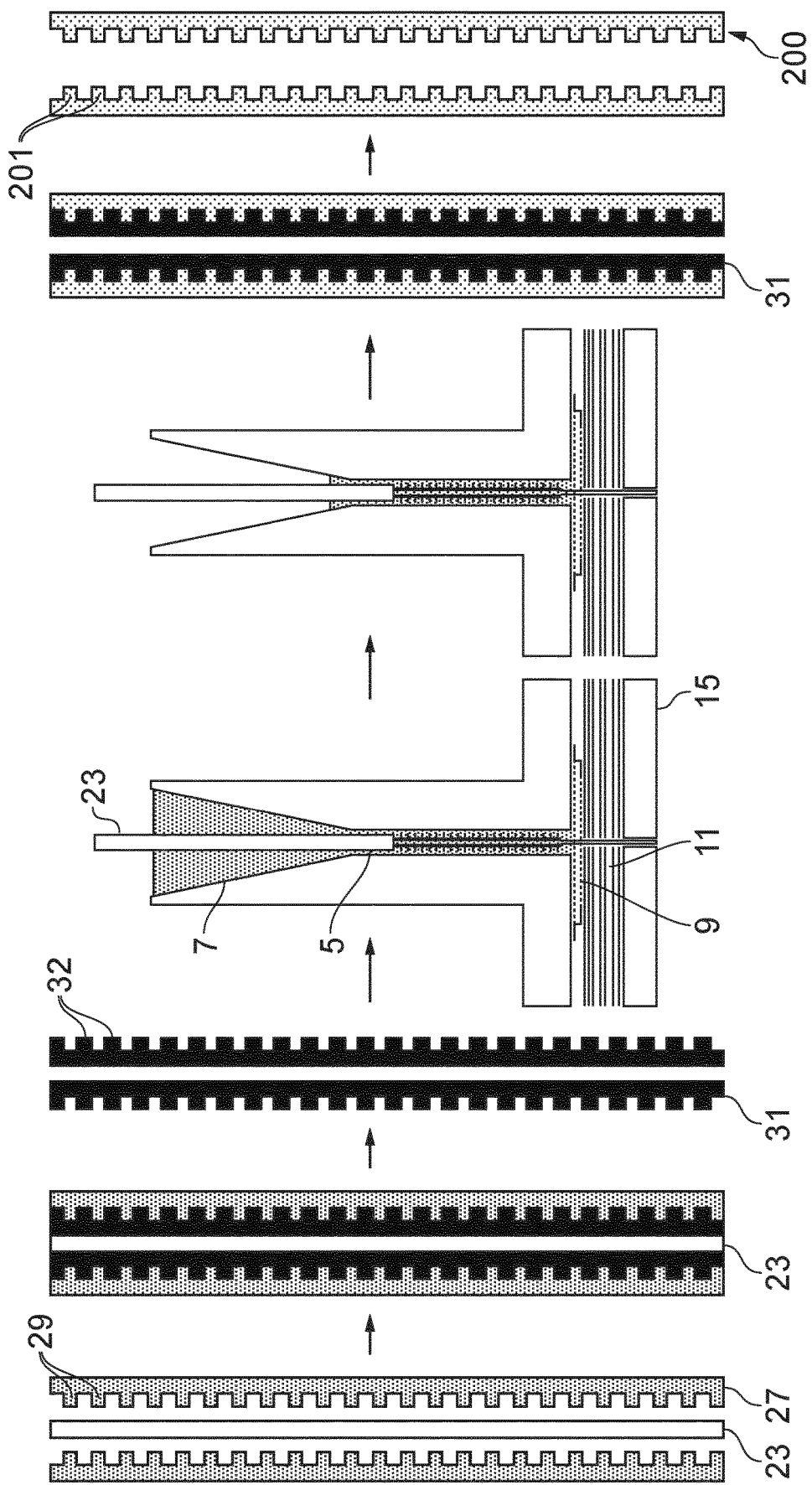
FIG. 4 is a schematic diagram showing formation of a tissue equivalent tubular scaffold having luminal patterning according to another embodiment of the invention.

FIG. 4 is a schematic diagram showing formation of a tissue equivalent tubular scaffold having luminal patterning according to another embodiment of the invention. Here, a patterning mould 27 is provided, which comprises a plurality of surface features 29 on an inner surface of the patterning mould. Conveniently, the patterning mould is 3D printed, which allows for a wide variety of surface features to be formed. The lumen template 23 is disposed within the patterning mould, and a patterning layer 31 is formed around the lumen template 23 using a patterning material. The patterning mould is then removed, e.g. by dissolution in an appropriate (selective) solvent. In this way the patterning mould can be removed without damage to the patterning layer. The result of this is that the lumen template comprises a patterned surface provided by the patterning layer 31, the patterned surface comprising a plurality of surface features 32, which are the inverse of the surface features 29 provided on the patterning mould. Here, the surface features are a plurality of recesses. The remaining method then proceeds as described above in relation to FIG. 1: the lumen template comprising a patterned surface is disposed within the casting chamber, and the casting material is cast around this and subsequently densified to provide a tissue equivalent tubular scaffold 200 comprising a patterned lumen, as the casting material infiltrates the pattern in the patterning layer. The patterned lumen here comprises a plurality of luminal projections 201 which are the inverse of the surface features 32 formed on the patterning layer. The patterning layer 31 is then removed from the tubular scaffold by heating of the scaffold to melt the patterning material, thus allowing it to flow out of the tubular scaffold.

Figure 5:
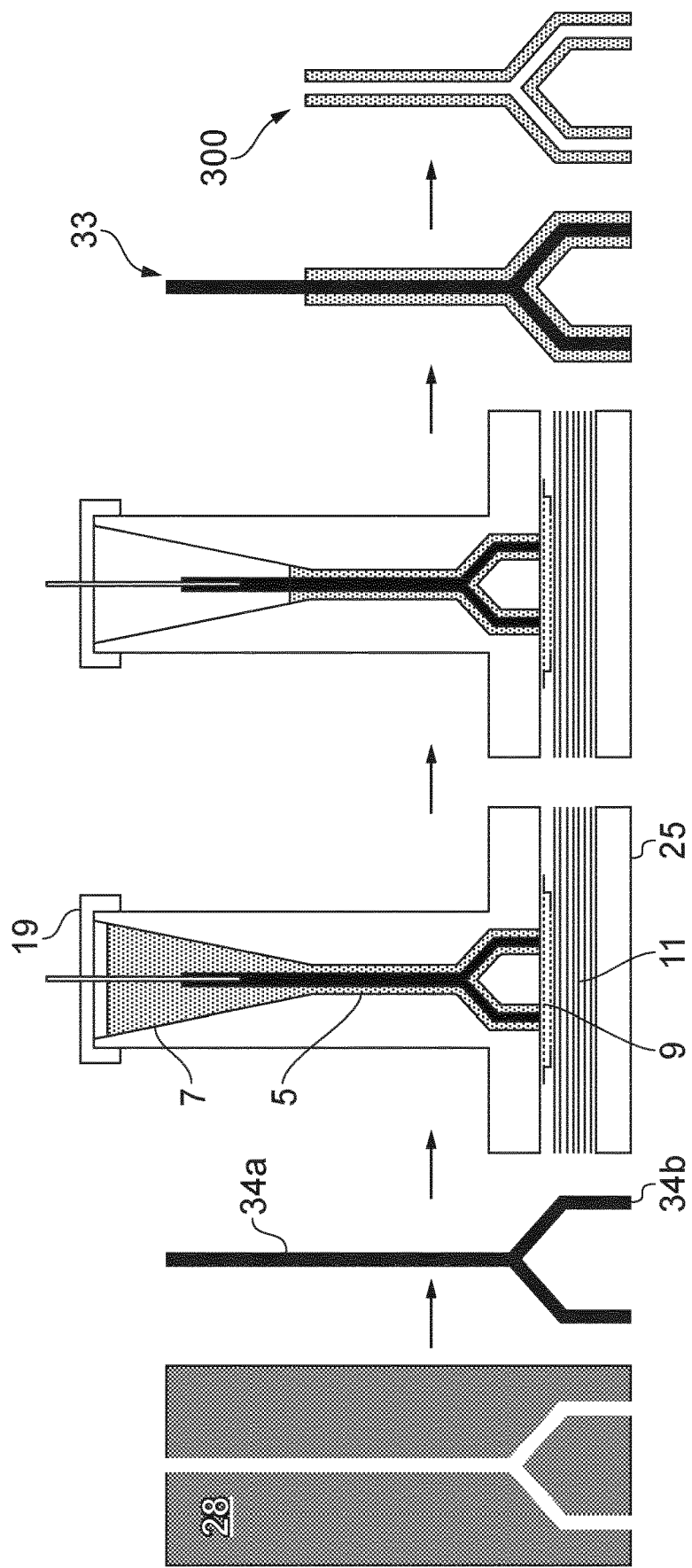
FIG. 5 is a schematic diagram showing formation of a bifurcating tissue equivalent tubular scaffold according to another embodiment of the invention.

FIG. 5 is a schematic diagram showing formation of a bifurcating tissue equivalent tubular scaffold according to another embodiment of the invention. Here, the lumen template 33 is a bifurcated rod, having a single 'parent' branch 34a and two 'daughter' branches 34b. The 'daughter' branches have a smaller diameter than the parent branch, although this is a design choice and is not essential. The lumen template is formed by casting from a template mould 28. Conveniently, the template mould 28 is 3D printed. After casting of the cote template within the template mould, the template mould is then removed, e.g. by dissolution in an appropriate (selective) solvent. In this way the template mould can be removed without damage to the lumen template 33. The remaining method then proceeds as described above in relation to FIG. 1 and FIG. 2: the bifurcated rod lumen template 33 is disposed within the casting chamber (here by affixing the lumen template to a supporting lid piece 19), and the casting material is cast around this and subsequently densified to provide a tissue equivalent bifurcated tubular scaffold 300.

The bifurcated lumen template 33 is then removed from the bifurcated tubular scaffold by heating of the scaffold to melt the lumen template, thus allowing it to flow out of the bifurcated tubular scaffold.

Figure 6:
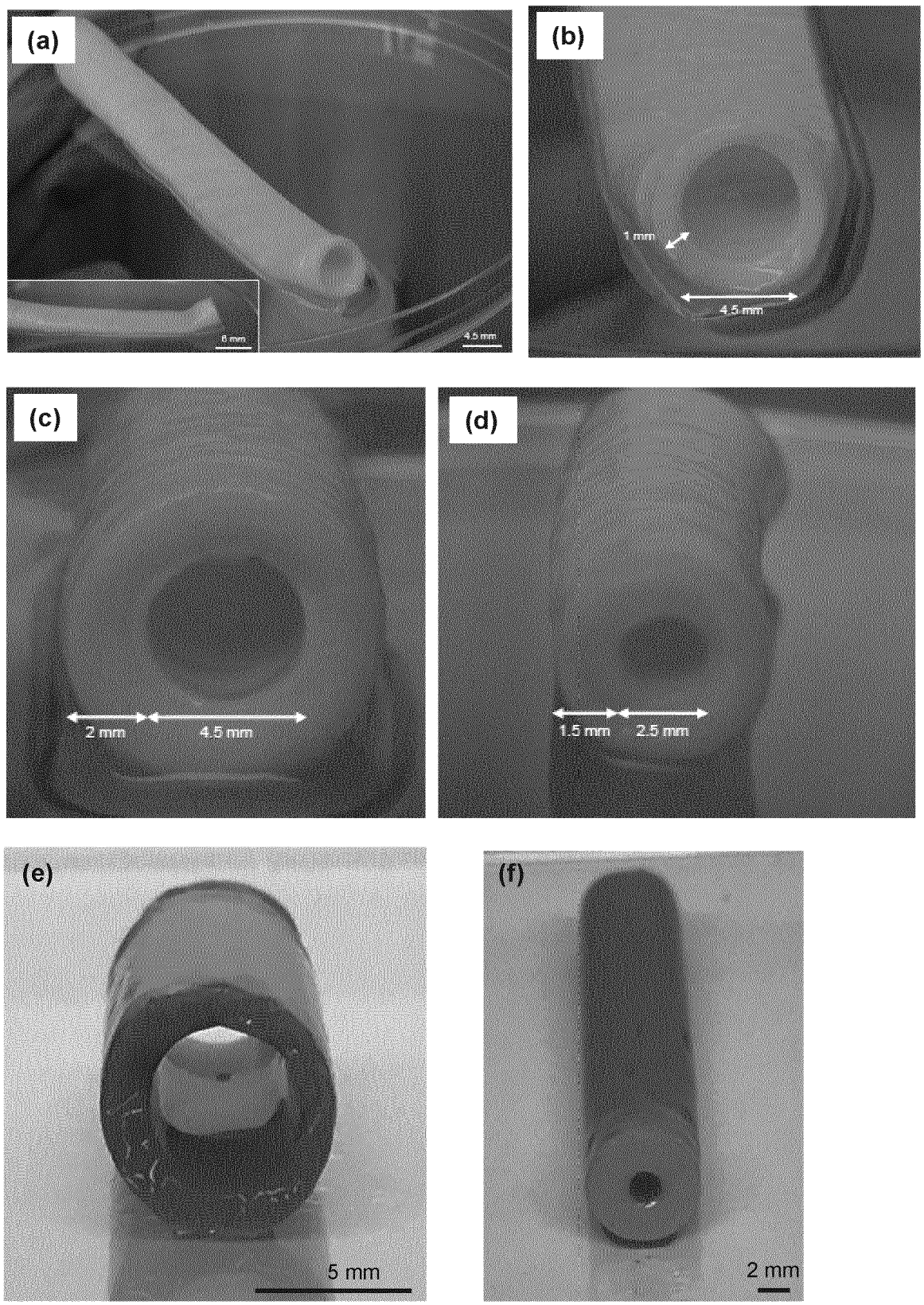
FIGS. 6 (a)-(i) show various images of densified collagen tubular scaffolds having a range of wall thicknesses and lumen sizes formed according to the method of the present invention, and (j) shows collagen fibril alignment in a tissue equivalent tubular scaffold manufactured according to the present invention, as shown using second harmonic generation microscopy, an arrow indicating 'hoop'/circumferential direction of the tubular scaffold.
Figure 6:
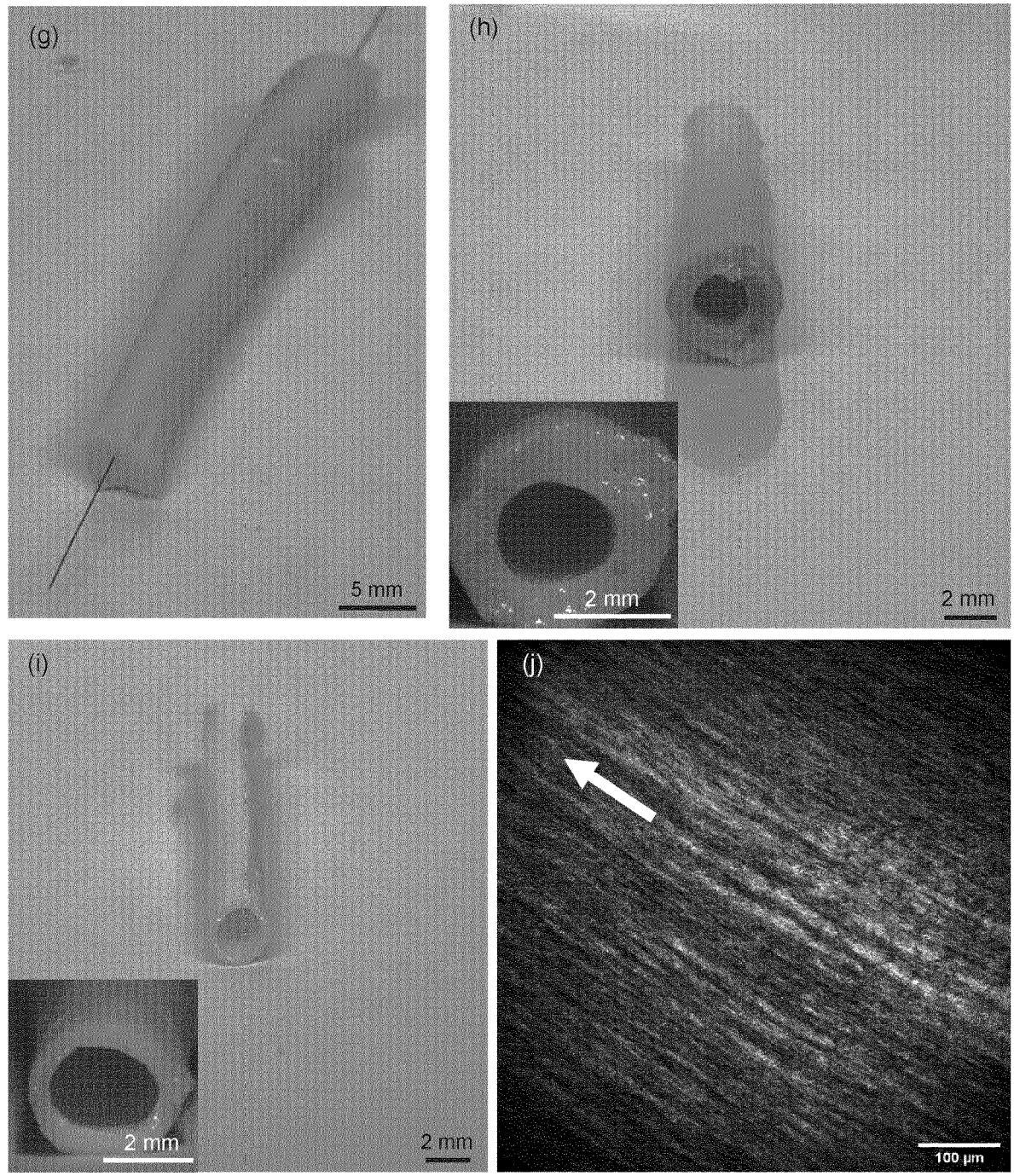

FIGS. 6 (a)-(i) show various images of densified collagen tubes (tubular scaffolds) having a range of wall thicknesses and lumen sizes formed according to the method of the present invention. FIGS. 6 (a) and (b) show the same scaffold from different angles. The scaffold has an inner diameter of 4.5 mm, and a wall thickness of 1 mm. FIG. 6(c) shows a densified collagen tube having an inner diameter of 4.5 mm, and a wall thickness of 2 mm. FIG. 6(d) shows a densified collagen tube having an inner diameter of 2.5 mm, and a wall thickness of 1.5 mm. FIG. 6(e) shows a densified collagen tube having an inner diameter of 5 mm and a 1.5 mm wall thickness. FIG. 6(f) shows a densified collagen tube having an inner diameter of 2 mm and a 2.5 mm wall thickness. FIG. 6(g) shows a densified collagen tube having an inner diameter of 50 μm, with a 2.5 mm wall thickness. As can be seen, tissue equivalent scaffold structures formed according to the present invention are self-supporting. Furthermore, they are seamless.

FIGS. 6(h) and (i) show the result of performing an additional evaporative drying step on densified collagen tubes produced according to the method of the present invention. Micrograph images of the resulting tubes are shown as an inset in each figure. Before evaporative drying, the densified collagen tubes had a 2.5 mm wall thickness. It was found that performing an additional evaporative drying step leads to finer wall thicknesses. The tube shown in FIG. 6(h) has a 2 mm luminal diameter with 1 mm wall thickness.

The tube shown in FIG. 6(i) has a 2 mm luminal diameter with 500 μm wall thickness. The resulting difference in wall thickness post-evaporative-drying was found to relate to initial collagen concentration: the tube shown in FIG. 6(h) was formed using a collagen gel having a concentration of 5 mg/ml (before densification), and the tube shown in FIG. 6(i) was formed using a collagen gel having a concentration of 2.5 mg/ml (before densification).

FIG. 6(j) shows collagen fibril alignment in a tissue equivalent tubular scaffold manufactured according to the present invention, as shown using second harmonic generation microscopy. Arrow denotes hoop direction.

Figure 7:
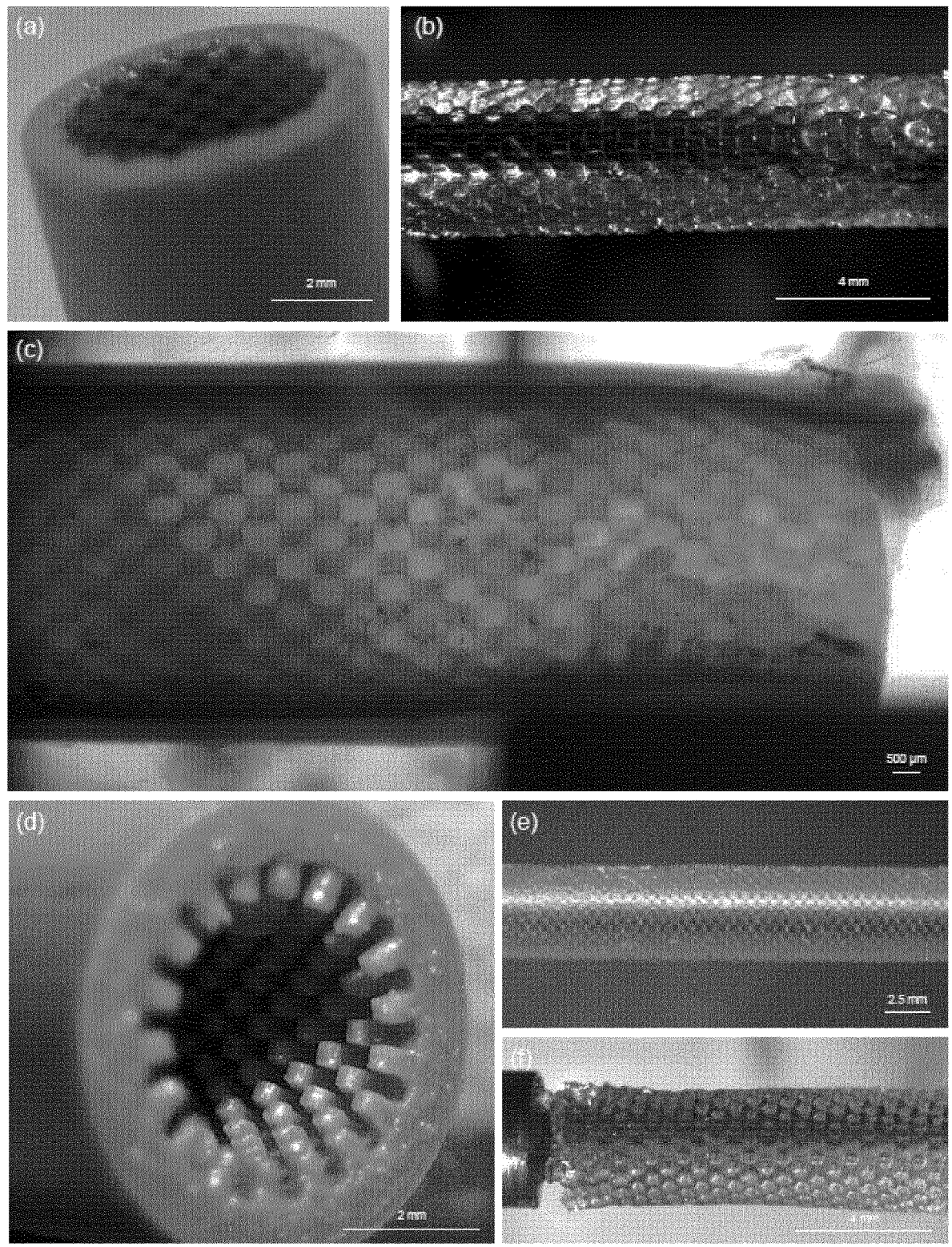
FIG. 7 shows: (a) a 3D printed wax mould for gelatin gel cast; (b) a gelatin gel inverse mould, displaying 500 µm surface features. (c) a densified collagen tubular scaffold with patterned lumen; (d) a 3D printed model containing surface feature; (e,f) examples of gelatin gel inverse moulds.

FIG. 7(a) shows a patterning mould in the form of a 3D printed wax mould. The mould comprises a series of surface features in the form of cubic recesses formed on an inner surface of the mould. This mould can be used in the production of a patterned lumen template. FIG. 7(b) shows a gelatin gel inverse mould (patterning layer) formed around a central rod. The gelatin gel layer comprises surface features which are about 500 μm long, and about 250 μm×250 μm, in cross section. FIG. 7(c) shows a densified collagen tube with patterned lumen. FIG. 7(d) shows a 3D printed patterning mould comprising surface features in the form of rod-like projections. FIGS. 7(e) and (f) show further examples of gelatin gel inverse moulds having a variety of surface features.

Figure 8:
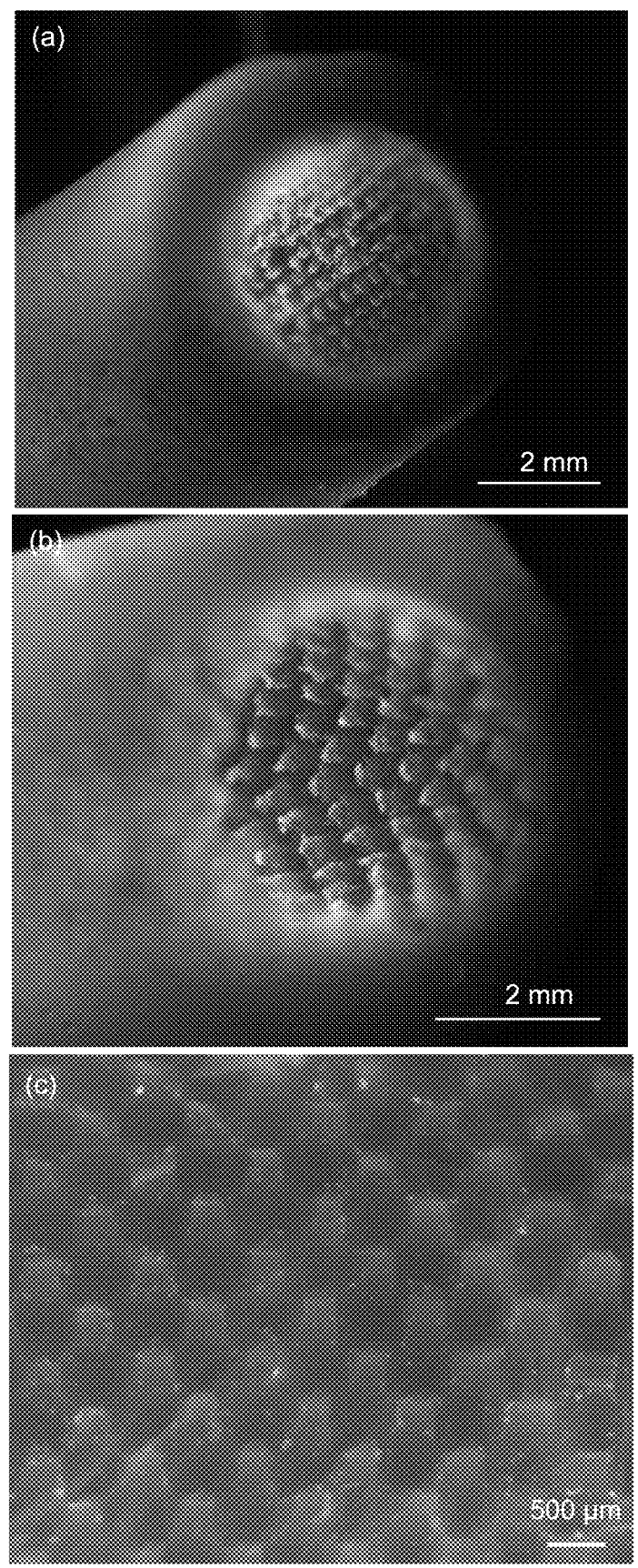
FIG. 8 shows (a) first, and (b) second images of a densified collagen tubular scaffold with patterned lumen, taken using a dissecting microscope using a fibre optic light source, in addition to (c) a higher-magnification image of the patterned lumen, showing regular pattern of villi-like structures.

FIGS. 8 (a), (b) and (c) are various images of a densified collagen tubular scaffold with patterned lumen, taken using a dissecting microscope using a fibre optic light source. A regular pattern of villi-like structures with cross-sections of 250 μm and heights of 500 μm can be seen. Such tubes may be particularly useful for intestinal applications, where the presence of crypt-villus structure on the luminal surface may promote efficient exchange of nutrients.

Methods according to the present invention will be described in greater detail below, in line with the following examples.

Section a—Fabrication of Densified Collagen Tube (Tubular Scaffold)

This method produces a uniaxial, densified collagen tube, suitable for cell seeding and implantation. More advanced methods, including surface patterning and bifurcating tubes may be built around this core method. This method is described in brief above in relation to FIG. 1.

Section a (i)—Assembly of Casting Chamber

A casting chamber, which comprises a funnel fluidly connected to a cylindrical elongate mould section was designed and assembled. The chamber comprises a flange for attachment to a second, base piece. In between these two parts, a porous membrane and paper towels were placed, and the casting chamber and base plate are screwed together. In this way, the cylindrical elongate mould section has a closed end part provided by the porous membrane.

1. CAD Models for the casting chamber were designed (e.g. Autodesk Inventor). The casting chamber was designed to include a funnel-shaped reservoir portion fluidly connected to a cylindrical elongate mould portion, to thereby allow for a relatively large volume of collagen gel to be densified into a cylinder/tube. Here, the internal diameter of the cylindrical section determines the outer diameter of final collagen tube (e.g. 1.5-10 mm). The funnel and cylinder were designed such that the internal volume of the casting chamber was 40 mL.

2. The casting chamber was machined out of Perspex™ acrylic.

3. A Perspex™ acrylic rod was chosen to serve as the lumen template for the casting chamber. The outer diameter of rod determines the inner diameter of the final collagen tube. The length was selected to be at least the sum of the heights of the funnel piece, base piece, and sufficient space for paper towels (e.g. 25 mm).

4. Sunflower oil was applied around the inner surfaces of the casting chamber, and the lumen template rod, to provide lubrication and prevent friction of collagen gel with chamber walls. Excess oil was removed by filling the chamber with water.

5. The central rod was mounted from below (i.e. through the membrane and paper towels). To achieve this, a base plate was designed comprising a central hole for mounting the central rod lumen template. Four M4 screw holes around the flange of the funnel piece and base allow for alignment and fixing of the two parts together.

6. A hole was made in a porous membrane (nylon, 0.2 µm pore size, hydrophilic), and a number of paper towels (approx. 25 mm thickness) using a biopsy punch of the same diameter as the lumen template.

The paper towels and porous membrane were placed over the lumen template rod and positioned near the base piece. The casting chamber was then attached to the base piece over the lumen template rod, so that the rod was axially disposed within the elongate mould portion of the casting camber, and so that the porous membrane closed the end of the elongate mould portion of the casting chamber. The porous membrane was held in place using waterproof adhesive tape).

Section a (ii)—Collagen Gel Preparation and Densification

The second task is to prepare the collagen precursor solution, pour it into the casting chamber, allowing the collagen to gel and the densification process to begin. When collagen solution is poured in the top of the funnel and gelled, the paper towels absorb the water through the membrane, which prevents the collagen fibrils from being absorbed but allows the water to pass. This absorption process pulls water out of the collagen gel and causes the fibrils to densify in the cylindrical elongate mould section. Once a predetermined fraction of water has been removed from the gel, the tube can be removed from the elongate mould portion of the casting chamber. Undertaking this process in a dry environment and at 37° C. (i.e. in a dry incubator) can help keep the paper towels dry by encouraging evaporation of removed water from the paper towels. Undertaking the process at room temperature may require more paper towels (or regular replacement) so as to not prematurely saturate.

1. Collagen gel precursor solution was prepared at both 2.5 mg/mL and 5 mg/mL final concentrations, for use in production of two different collagen scaffolds according to the following method. In order to form a gel, the collagen solution was neutralised and the ionic content raised by adding 10× cell medium, sodium bicarbonate solution and 1 M NaOH, which was then diluted with cell medium to achieve the correct final collagen concentration (Penicillin/Streptomycin and Amphotericin B are added as well). The solution was prepared using cold (4° C.) reagents, and was thoroughly mixed by shaking, before being centrifuged (1000 g, 5 min) to remove air bubbles. If required, cells can be incorporated at this stage to encapsulate cells in the walls of the final collagen tube. The collagen gel precursor solution was then poured into the casting chamber such that a portion of the rod lumen template extends above the casting material, filling the cylindrical elongate mould portion and partly filling the funnel-shaped reservoir portion.

2. A sheet of Parafilm™ was fixed over the top of the funnel portion of the casting chamber to prevent evaporation from the top of the collagen gel.

3. The collagen gel precursor solution then was left to gel to form the gel casting material at room temperature (slow), although some examples, the collagen gel precursor was left to gel in a 37° C. incubator (fast).

4. Water was allowed to flow out of the casting chamber through the porous membrane, thereby densifying the collagen gel remaining in the casting chamber. This continued until the collagen surface was observed to drop through the bottom of the funnel-shaped reservoir portion of the casting chamber and to the lower part of cylindrical elongate mould. Typically this step took 12-48 hours at room temperature, and 6-12 hours at 37° C., depending upon degree of friction between collagen gel and chamber walls, and volume of collagen to be densified.

5. The densified collagen tube was removed from the casting chamber by removing the screws holding the base piece to the casting chamber, and, using the central rod, pushing the tubular scaffold from the elongate mould portion.

6. Excess collagen was removed from the bottom of the tubular scaffold using a scalpel.

7. The collagen tube was stored in a 50 mL Falcon tube containing PBS with Penicillin/Streptomycin (antibiotic) and Amphotericin B (anti-fungal).

Section B—Fabrication of a Patterned Lumen Collagen Tube (Tubular Scaffold)

This method can be used to incorporate a pattern onto the internal surface of the densified collagen tubes. This has a range of potential applications, including potentially enhanced cell seeding and the inclusion of luminal structures found in native tubular structures, such as villi. The method discussed below uses a 3D printed and removable model material to cast a gelatin gel structure around a metal rod consisting of two diameters (such that the gelatin lies flush with the larger diameter surface. Having modified the central core template structure with this gelatin gel, the collagen densification process continues as in Section A (gel densification step performed at room temperature). This method is described in brief above in relation to FIG. 4.

Section B (i)—Preparation of Removable 3D Printed Patterning Mould and Assembly of Casting Chamber.

1. A CAD model was designed consisting of a hollow tube, with required luminal pattern on the inside, and an aperture. The inner diameter of the model tube determines the diameter of the densified collagen tube lumen (the outside diameter of the collagen tube is still determined by the elongate mould portion of the 3D printed casting chamber as described in Section A). One end of the model tube comprises an aperture which aligns a central rod to the centre of the 3D printed patterning mould. This rod is thinner (e.g. 1.5 mm) at the end mounting the 3D printed model, and the remaining length the same as the central rod lumen template used in Section A. This provides support to the gelatin gel patterning material during the collagen densification process.

2. This design was subsequently 3D printed in a removable model material (Solidscape 3D printing machines) to form a patterning mould. These machines have a very high resolution and can produce structures of 250 μm sizes. In order to achieve this, a support material was printed alongside the model material, and subsequently dissolved away using a proprietary selective solvent at 55° C. (in an oven), over several days.

3. The internal features of the 3D printed patterning mould were further cleaned by injecting warm selective solvent in the top of the patterning mould, using a 1 mL pipette to thereby remove loose debris from the surface features. The inner surface of the patterning mould was inspected under a microscope to check that debris had been suitably removed. The patterning mould was then dried to remove the selective solvent and placed in a container containing PBS. The tube was lightly tapped and the 3D printed mould perfused using a pipette to free any trapped air bubbles.

4. At this stage, the casting chamber was assembled as discussed above in Section A(i), with some minor differences. The base piece was 3D printed with a central hole sized fit the thinner metal rod (e.g. 1.65 mm diameter). The membrane and paper towels were prepared using a smaller biopsy punch (e.g. 1.5 mm diameter) so as to tightly fit the thinner metal rod.

Section B (ii)—Preparation of a Gelatin Mould for Surface Features

1. A 20% (w/v) solution of porcine gelatin (high Bloom) in PBS (no Calcium) containing Penicillin/Streptomycin and Amphotericin B was prepared. Use of 20% (w/v) gelatin may offer improved gel strength. Alternatively, use of 10% (w/v) gelatin may offer reduced swelling.

2. The gelatin, 3D printed patterning mould, and central rod were heated to 55° C. (in an oven).

3. Gelatin solution was poured into a 50 mL Falcon tube container. The solution was centrifuged at 1000 g for 1 minute to remove any air bubbles from pouring. The 3D printing patterning mould was placed in the gelatin solution. Gentle suction using a pipette was used to pull gelatin through the 3D printed patterning mould and liberate any air bubbles. Further, the container was tapped to help to free air bubbles. The central rod was then inserted through the 3D printed patterning mould, and the rod and patterning material (cast gelatin) were transferred for storage in a fridge (4° C.) for 1-24 hours to gel the gelatin patterning material.

4. The patterning mould was then dissolved using a selective solvent of 100% acetone to reveal the lumen template central rod comprising a gelatin patterning layer. The lumen template was inspected and any excess gelatin removed using tweezers.

5. The lumen template comprising gelatin patterning layer was then transferred to a PBS bath to remove any residual acetone and liberate any trapped air bubbles from the surface.

Section B (iii)—Mounting of Pattered Lumen Template and Removal of Densified Lumen Patterned Collagen Tube from Casting Chamber.

1. The lumen template comprising gelatin patterning layer was then disposed within the elongate mould portion of the casting chamber, by fitting the metal rod into the holes at the centre of the membrane, paper towels, and base piece.

2. The collagen gel casting and densification process then continued in a similar manner as described above in Section A, undertaken at room temperature (24-48 hours). After filling the casting chamber with the collagen gel, the chamber was tapped to improve infiltrate the collagen into small surface features in the gelatin gel and liberate any trapped air bubbles.

After densification of the collagen gel, the densified collagen tube was removed from the densification chamber and placed it in a 50 mL Falcon tube containing PBS, as described in Section A.

3. To remove the gelatin patterning layer, the 50 mL Falcon tube containing the densified collagen tube was placed in a 37° C. water bath for 1-2 hours, thus melting the gelatin gel, which diffuses away into the PBS, leaving the densified collagen tube with luminal surface features. The collagen tube was then removed from the 50 mL Falcon tube, and excess collagen removed using a scalpel.

Section C—Fabrication of a Bifurcating Densified Collagen Tube (Tubular Scaffold)

A bifurcating collagen tube can be fabricated using a gelatin gel mould as the central core template. This bifurcating tube can be made with a parent branch of differing diameter to the daughter branches (which potentially can be different diameters from each other). The gelatin gel core template is made by casting in a 3D printed mould, made of two halves which are screwed together, necessary to position the bifurcating gelatin gel as the central core template. The collagen gel densification then continues as in Section A and B. This method is described in brief above in relation to FIG. 5.

Section C (i)—Fabrication of Lumen Template Mould and Bifurcated Lumen Template

1. A lumen template mould was 3D printed (e.g. Ultimaker 2+, PLA/ABS filament) consisting of two halves and a bifurcating channel down the middle. These two halves were screwed tightly together and a 19 G hypodermic stainless steel tube pushed into the end, which was used to infiltrate gelatin into the channels, and to subsequently mount the gelatin mould in the casting chamber.

2. This 3D printed mould, hypodermic tube, and 10-20% (w/v) gelatin gel were heated to 55° C. (in an oven).

3. Liquid gelatin was injected into lumen template mould using a 20 mL syringe, and the hypodermic tube mounted in the far end. The filled mould was stored horizontally at room temperature for approximately 10 minutes to allow the gelatin gel to set, before removing the needle and syringe. The lumen template mould was placed in the fridge (4° C.) for a further 1 hour-overnight to allow the gelatin gel strength to increase.

4. The screws were removed from the lumen template mould and the two halves of the mould prized apart. The gelatin gel lumen template, mounted on the hypodermic tube, was removed from the mould using tweezers.

Section C (ii)—Design of New Casting Chamber and Assembly with Gelatin Core Template 1. A new casting chamber was designed and 3D printed. The casting chamber comprises a funnel-shaped reservoir portion fluidly connected to a bifurcated elongate mould portion. Further, a lid for the casting chamber was designed and printed. The gelatin lumen template was supported by feeding the hypodermic tube, mounting the gelatin template, through a hole in the supporting lid piece of the casting chamber (this is shown schematically in FIG. 5).

2. The casting chamber here was made from two halves joined together. A layer of waterproof adhesive tape was mounted between the two halves of the casting chamber to help prevent leakage of casting material from the casting chamber.

3. The height of the hypodermic tube supporting the bifurcating lumen template was adjusted to position the lumen template such that the daughter branches of the lumen template were disposed within corresponding branches of the bifurcated elongate mould portion of the casting chamber. The bottom of the daughter branches were flush with the closed end of the casting chamber, provided by the porous membrane.

Section C (iii) Densification and Removal of Bifurcating Collagen Tube from Densification Chamber.

1. The densification process continued as described in Section A (performed at room temperature for 24-48 hours).

2. Once the densification process was complete, the casting chamber was disassembled and the hypodermic tube removed from the top of the lumen template. The densified collagen tube containing the gelatin bifurcated lumen template was placed in a 50 mL Falcon tube containing PBS with Penicillin/Streptomycin and Amphotericin B.

3. The Falcon tube was subsequently placed in a 37° C. water bath. Over 1-2 hours, the gelatin gel template melted and diffused away into the PBS, leaving a bifurcating densified collagen tube.

4. Excess collagen was removed using a scalpel.

Section D—Densified Collagen Tube Seeding of Luminal Surfaces with HeDG2 Cells

Figure 9:
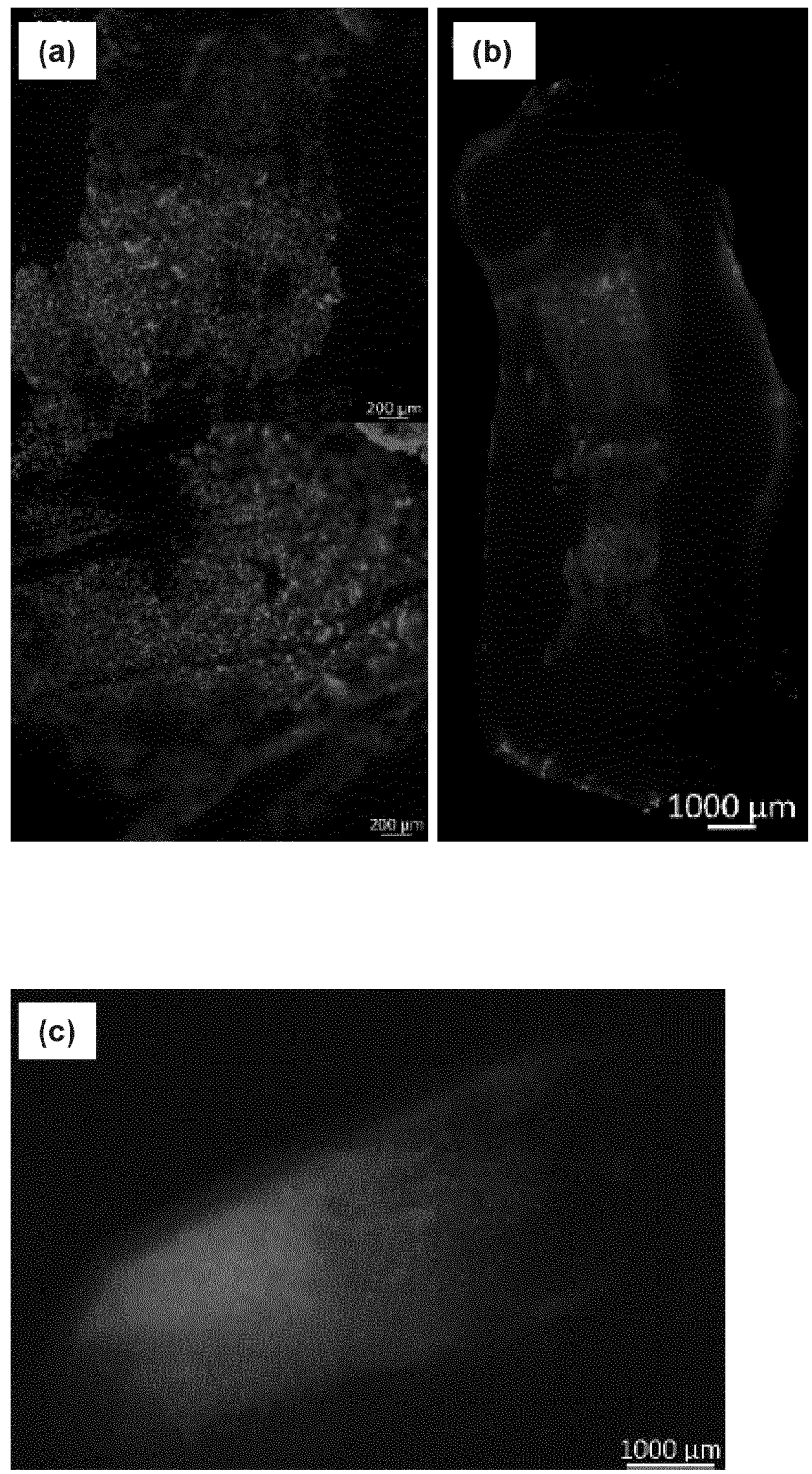
FIG. 9 shows: (a,b) HepG2s cell attachment to a scaffold after 1 week (Calcein AM live stain); (c) mCherry-stained HepG2s on a scaffold after 2 days of culture.

In order to show that the collagen tubes allow for cell attachment, they were seeded them with HepG2 cells. Using two metal hollow cylinders filled with hydrophilic membrane, the tube was filled with cells and time allowed for their attachment, while medium from the surrounding reservoir was allowed to exchange with medium in the lumen. Results of cell seeding are shown in FIG. 9, and discussed below.

1. Two short sections of metal hypodermic tubing were cut and the surfaces ground to be substantially smooth. The diameter of metal tubing was selected to match the collagen tube to be seeded.

2. A semi-circle of nylon membrane (5 μm pore size) was cut and folded into a cone. This was inserted into the metal tubes using tweezers. Excess membrane was removed from each end, using scissors.

Two lengths of suturing wire were cut. These parts were autoclaved.

3. HepG2s were grown in T75 flasks until confluent (DMEM with 10% FBS and 1% Pen-Strep).

4. 50 mL of cell medium was transferred to an 80 mm petri dish.

5. The collagen tube was cut to the required length using a scalpel. One of the metal tubes was inserted into one end of the collagen tube and tied in place using the suture wire, before being placed into the petri dish.

6. Cells were trypsinized and centrifuged as normal, in a 15 mL Falcon tube. Having removed the supernatant, the cells were re-suspended in 30 μL of cell medium.

7. A second loop of suture and metal tube (containing membrane) were prepared and placed near the second end of the collagen tube.

8. The collagen tube was filled with cells using a 100 μL pipette, before the second metal tube was inserted into the collagen tube and tied in place with a suture loop. Excess suture wire was removed using scissors.

9. The collagen tube was rotated about its longitudinal axis after 4 hours to allow cell seeding on the top surface.

10. After another 4 hours, the metal cylinders were removed from the ends of the collagen tube using tweezers. The tubes were cultured further under static culture conditions, although active flow through perfusion is possible at this point.

11. Cells were imaged using a fluorescent microscope (mCherry-positive cells or Calcein AM live stain).

FIGS. 9(a) and (b) show HepG2s cell attachment after 1 week (Calcein AM live stain). A section of collagen tube was cut and unwrapped, and was found to contain two large confluent regions of HepG2s. FIG. 9(c) shows mCherry-stained HepG2s after 2 days of culture.

FIG. 14(a) shows a schematic of surface seeding process described in this section.

Figure 14:
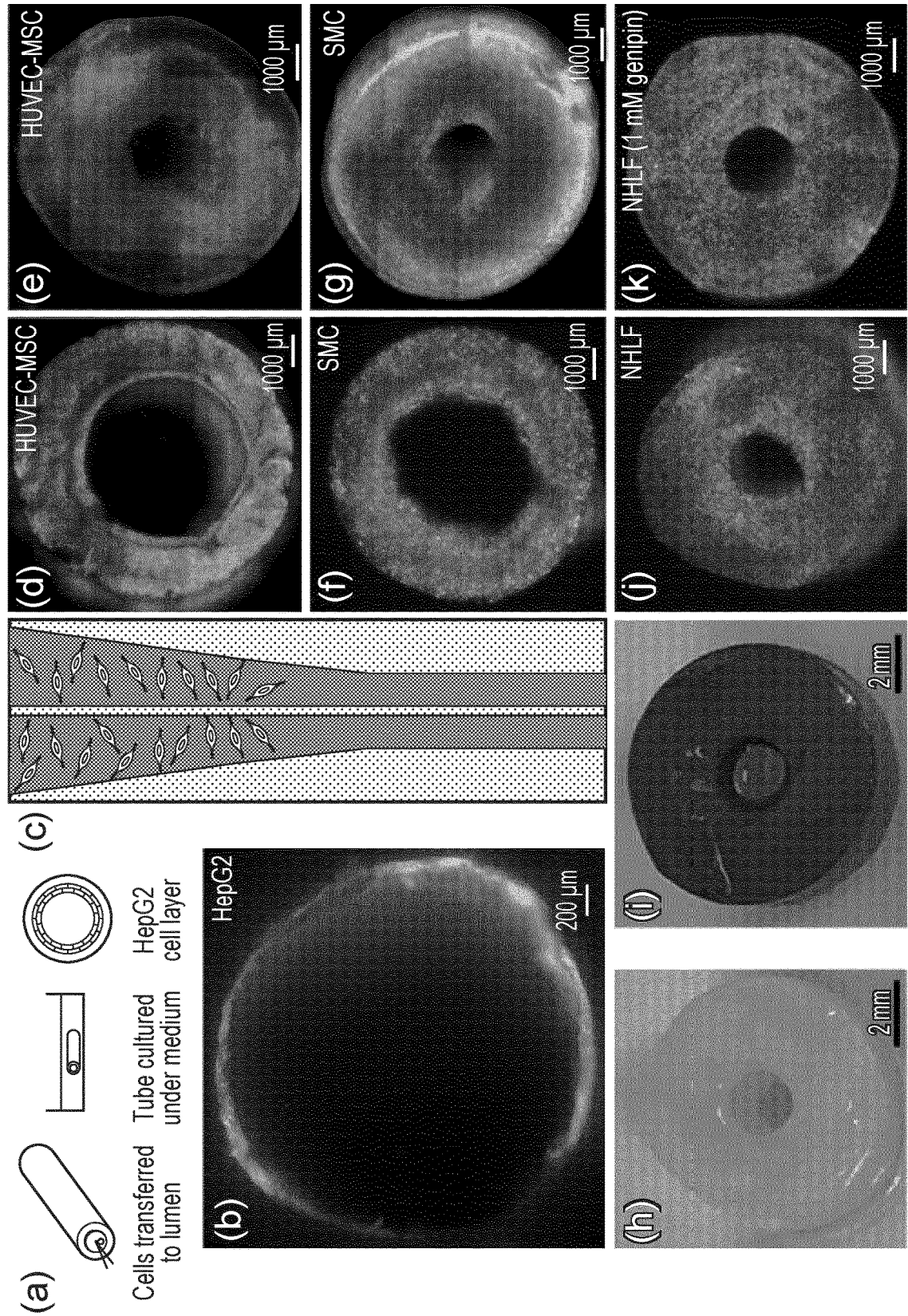
FIG. 14 shows: (a) a schematic of a luminal surface cell seeding process; (b) formation of a monolayer of cells on the luminal surface resulting from a luminal cell seeding process; (c) a schematic showing a bulk cell seeding process, with cells mixed into the top half of the precursor gel solution; (d)-(k) various images of cell-seeded collagen tubes.

FIG. 14 (b) shows that this surface seeding process led to formation of monolayer of cells on the luminal surface.

Section E—Further Investigations into Densified Collagen Tube Seeding

Human liver cancer cell line (HepG2s) were cultured in DMEM+10% FBS. Green fluorescent protein (GFP) and Red Fluorescent Protein (RFP) human umbilical vein endothelial cells (HUVECs, Promocell), normal human lung fibroblasts (NHLFs, Promocell) and mesenchymal stem cells (MSCs, Promocell) were cultured in their respective proprietary mediums (Promocell). Immature smooth muscle cells (SMCs) were cultured in serum-free medium until maturity and then were subsequently grown in standard medium. Cells were cultured until 90% confluency and detached from T75 flasks using TrypLE (Life Technologies). Cells were centrifuged at 250 g for 5 min and counted using a haemocytometer.

Densification experiments where cells were encapsulated into the walls of the tubes were performed at $2-8\times10^6$ cells per tube (i.e. $1-4\times10^5$ cells/mL for 20 mL precursor solution), using collagen tubes with luminal diameters of 2 mm and 5 mm. Tubes with cells encapsulated in the bulk of the tubes were prepared using HepG2s, NHLFs, GFP HUVECs and RFP HUVECs, and SMCs. The collagen precursor solution was prepared as above, subtracting a volume for the addition of cells later, and was subsequently centrifuged at 4000 g for 10 min. 2-3 mL of collagen, without cells, was poured into the casting chamber to fill the elongate mould portion. Doing so prevents the clogging of the porous membrane with cells. A resuspended cell pellet was then pipetted on top of the precursor gel solution. Using a sterile metal spatula, the cells were then slowly mixed into the gel precursor solution until uniform, and the solution was then poured into the funnel assembly as described above. For experiments with cells seeded into the bulk of the collagen gel, the funnel assembly was transferred to a 37° C. incubator for rapid gelation. FIG. 14 (c) is a schematic showing this bulk cell seeding process, with cells mixed into the top half of the precursor gel solution.

For densified collagen tubes with two distinct cell domains, two 10 mL collagen precursor solutions were prepared. 1.5 mL from each was poured into the cylindrical section. GFP and RFP HUVECs were subsequently stirred into their respective precursor solutions and slowly poured into the chamber, one after the other. As with above, the casting chamber assembly was transferred to a 37° C. incubator straight after assembly to prevent sedimentation and cell mixing.

Cell characterisation was performed via calcein AM staining (Life Technologies). For bulk seeding experiments, the cells were either stained prior to encapsulation or after the densification process. Briefly, calcein AM was resuspended at 4 mM in PBS. Cells plated in T75 flasks, or cell-seeded tubes, were washed in PBS and incubated in a 4 µM calcein AM solution in PBS, at 37° C. for 20 min. For luminal surface seeding experiments discussed in section D, above, HepG2s were stained prior to seeding. Cell-ladened tubes were imaged using an epi-fluorescence microscope (Zeiss Axio-Observer.Z1).

FIG. 14(d)-(k) show various images of cell-seeded collagen tubes. All cells were stained using calcein AM (green). FIG. 14 (d) shows HUVECs encapsulated in the walls of a 5 mm luminal diameter tube. FIG. 14 (e) shows HUVECs encapsulated in the walls of a 2 mm luminal diameter tube. FIG. 14 (f) shows SMCs encapsulated in the walls of a 5 mm luminal diameter tube. FIG. 14 (f) shows SMCs encapsulated in the walls of a 2 mm luminal diameter tube. FIG. 14 (h) shows an uncrosslinked NHLF-seeded 2 mm luminal diameter tube. FIG. 14 (i) shows a NHLF-seeded 2 mm luminal diameter tube after 1 mM genipin crosslinking.

It can be seen from these images that these cell seeding studies yielded tubes in which cells were uniformly distributed through the walls of the tubes, for both 2 mm and 5 mm wall thicknesses. Genipin caused a significant colour change in the densified collagen tubes (contrast FIGS. 14(h) and (i)).

To test the biocompatibility of the crosslinker, a cellularised densified collagen tube was immersed in a 1 mM genipin solution for 24 h. FIGS. 14 (j) and (k) show NHLF-seeded 2 mm luminal diameter tubes showing high viability of cell population (j) before and (k) after this 24 h 1 mM genipin crosslinking.

Section F—Tensile Testing of Densified Collagen Tubes

Tensile testing was carried out with an Instron desktop testing machine, fitted with a 5N load cell. The tubular wall was "unwrapped" so that it was planar, by cutting along the long axis of the tube. A metal cutter was machined to generate rectangular, dog-bone specimens along the long axis of the tubes, with gauge sections 7 mm long, 3 mm wide and 1.5 mm thick. The specimens were mounted, using superglue, in paper tabs with a central cut-out. The tabs were gripped in the jaws of the testing machine and, prior to testing, cuts were made from each side of the central cut-out. The crosshead displacement was measured using a linear variable differential transformer (LVDT). All tests were conducted in displacement control at a rate of 1 mm/min. The Young's modulus was measured from the tangent slope of the nominal stress-strain curve up to 2% strain.

The results of this tensile testing are shown in FIG. 15-18. For results in this section relating to genipin-crosslinked tubular scaffolds, the tubular scaffolds were crosslinked using the methodology described in 'Section G—Effect of genipin-crosslinking on stability in acidic conditions', below.

Figure 15:
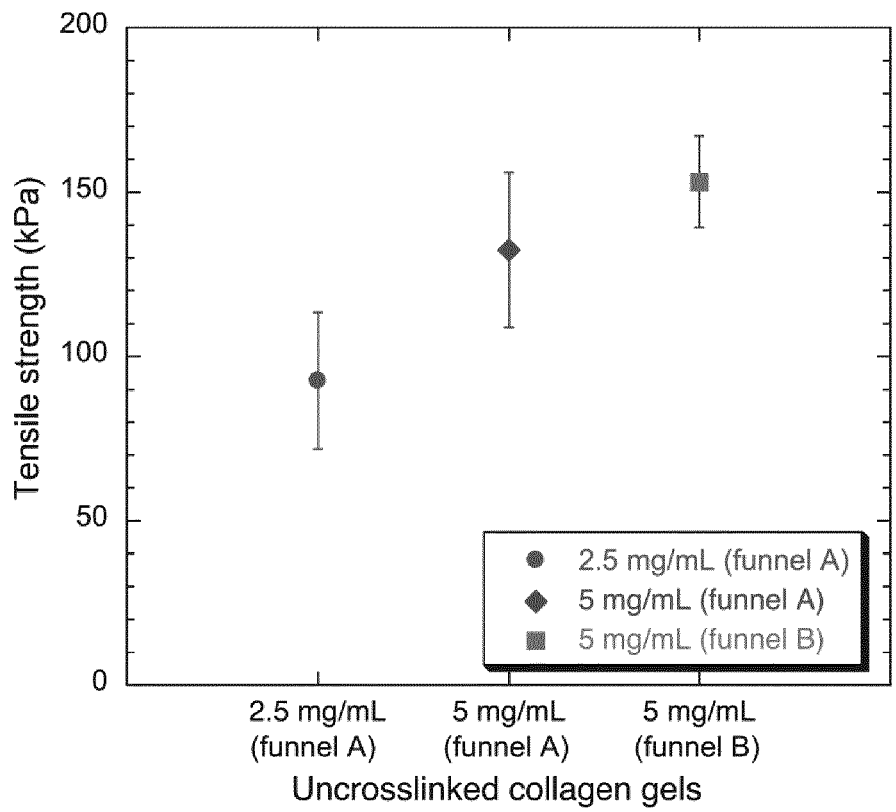
FIG. 15 is a graph of measured tensile strength for uncrosslinked collagen tube samples, for a range of initial collagen concentrations and for tubular scaffolds formed using the casting chambers shown in FIG. 11(a) (Funnel A) and FIG. 11(b) (Funnel B).

FIG. 15 is a graph of measured tensile strength for uncrosslinked collagen tube samples, for a range of initial collagen concentrations and for tubular scaffolds formed using the casting chambers shown in FIG. 11(a) (Funnel A) and FIG. 11(b) (Funnel B).

Figure 16:
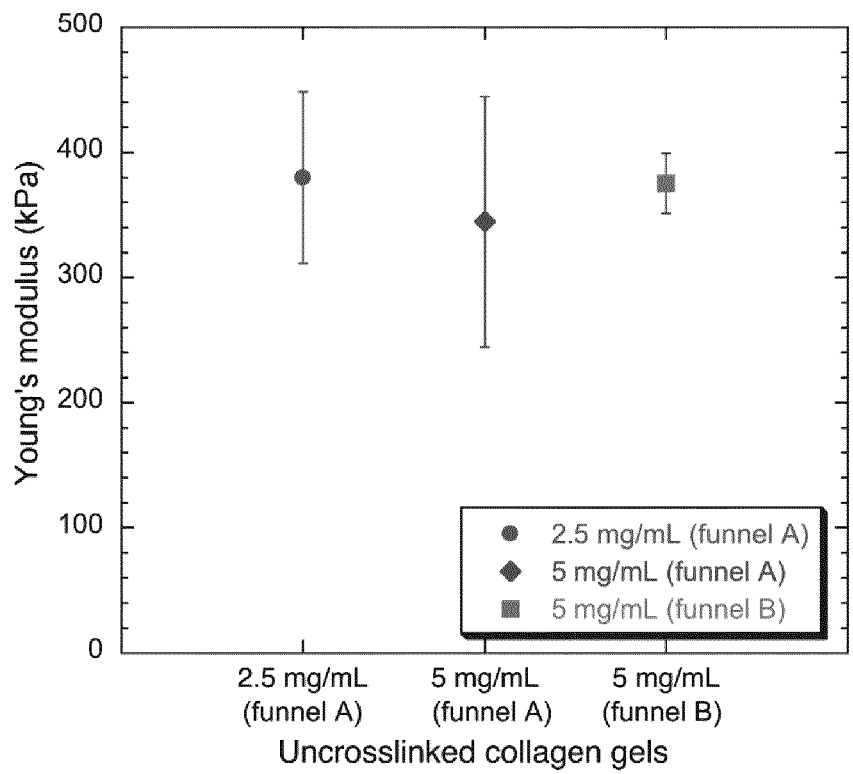
FIG. 16 is a graph of measured Young's modulus for uncrosslinked collagen tube samples, for a range of initial collagen concentrations and for tubular scaffolds formed using the casting chambers shown in FIG. 11(a) (Funnel A) and FIG. 11(b) (Funnel B).

FIG. 16 is a graph of measured Young's modulus for uncrosslinked collagen tube samples, for a range of initial collagen concentrations and for tubular scaffolds formed using the casting chambers shown in FIG. 11(a) (Funnel A) and FIG. 11(b) (Funnel B).

Figure 17:
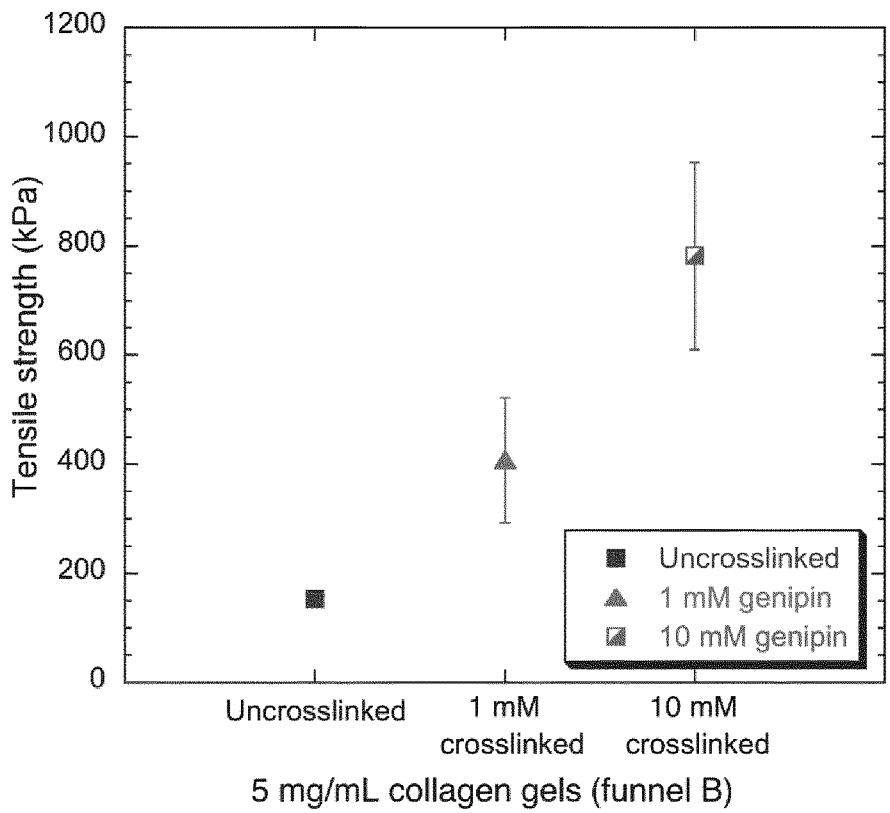
FIG. 17 is a graph of measured tensile strength for tubular scaffolds formed from 5 mg/mL initial collagen concentration formed using the casting chamber shown in FIG. 11(b) (Funnel B), comparing uncrosslinked, 1 mM genipin crosslinked, and 10 mM genipin crosslinked samples.

FIG. 17 is a graph of measured tensile strength for tubular scaffolds formed from 5 mg/mL initial collagen concentration formed using the casting chamber shown in FIG. 11(b) (Funnel B), comparing uncrosslinked, 1 mM genipin crosslinked, and 10 mM genipin crosslinked samples.

Figure 18:
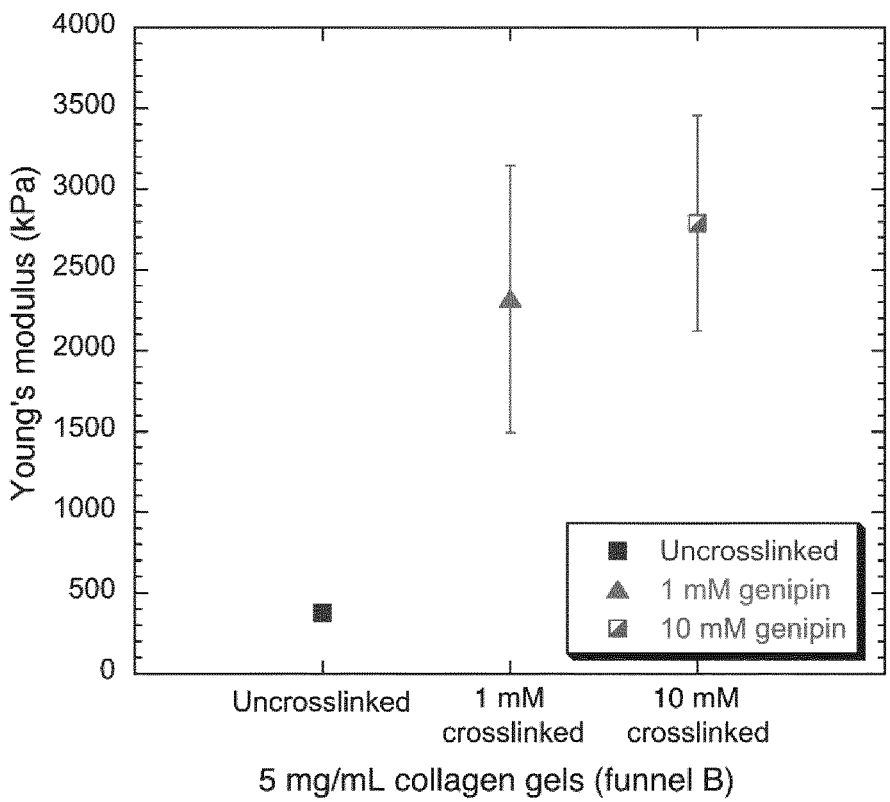
FIG. 18 is a graph of measured Young's modulus for tubular scaffolds formed from 5 mg/mL initial collagen concentration formed using the casting chamber shown in FIG. 11(b) (Funnel B), comparing uncrosslinked, 1 mM genipin crosslinked, and 10 mM genipin crosslinked samples.

FIG. 18 is a graph of measured Young's modulus for tubular scaffolds formed from 5 mg/mL initial collagen concentration formed using the casting chamber shown in FIG. 11(b) (Funnel B), comparing uncrosslinked, 1 mM genipin crosslinked, and 10 mM genipin crosslinked samples.

The results showed that the initial collagen concentration, the choice of funnel geometry and the crosslinker concentration each influence the strength of the tubes. The tensile strength was found to increase with starting collagen concentration (hence final collagen concentration) and also with genipin crosslinker concentration (see FIGS. 17 and 18). Higher strength was observed for collagen tubes produced using the casting chamber shown in FIG. 11(b) (Funnel B) compared to those produced using the casting chamber shown in FIG. 11(a) (Funnel A). The Young's modulus was found to be very similar for uncrosslinked collagen over the concentrations tested, and was found to increase with crosslink density (i.e. crosslinker concentration).

Section G—Effect of Genipin-Crosslinking on Stability in Acidic Conditions

Genipin (Bioserv UK) was resuspended in sterile PBS at 1 and 10 mM concentrations. Samples of densified collagen tube were immersed in genipin solutions and placed on an orbital shaker for 24 h at room temperature, followed by a further 24 h in sterile PBS. Biocompatibility testing of 1 mM genipin solutions with collagen tubes seeded with cells was performed using cell medium containing dissolved genipin. Tubes were immersed in cell medium containing genipin and left in an incubator at 37° C. for 24 h.

To test the effect of genipin-crosslinking on stability in acidic conditions, samples were cut from uncrosslinked and genipin-crosslinked densified collagen tubes fabricated according to the present invention. These were immersed in 100 mM acetic acid solution, alongside samples of excised vena cava (Medical Meats).

A change in mass was measured over a 2 h period for uncrosslinked samples and over several days for crosslinked tube and excised vena cava samples, using a mass balance with a precision of 0.1 mg and removing the fluid at regular timepoints. As the uncrosslinked samples swelled and dissolved, it was not possible to reliably remove all the surrounding fluid without also removing the dissolving collagen.

Figure 19:
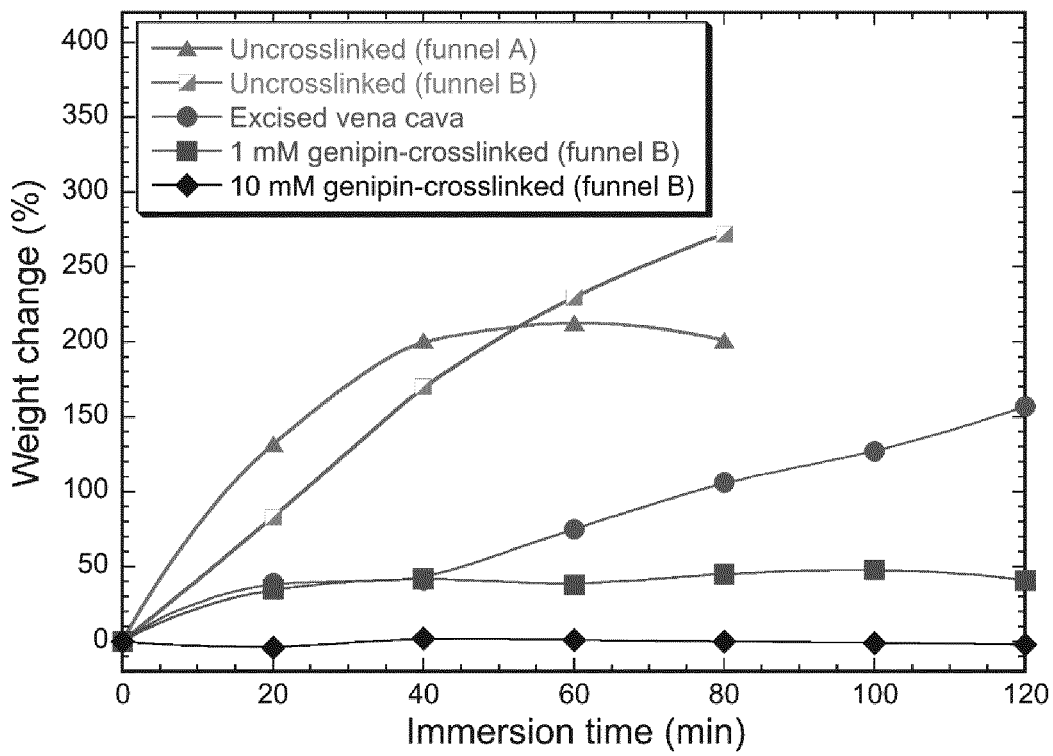
FIG. 19 is a graph showing percentage change in weight over a 2 h period, for crosslinked and uncrosslinked tube samples, and excised vena cava.

FIG. 19 is a graph showing percentage change in weight over a 2 h period, for crosslinked and uncrosslinked tube samples, and excised vena cava.

Figure 20:
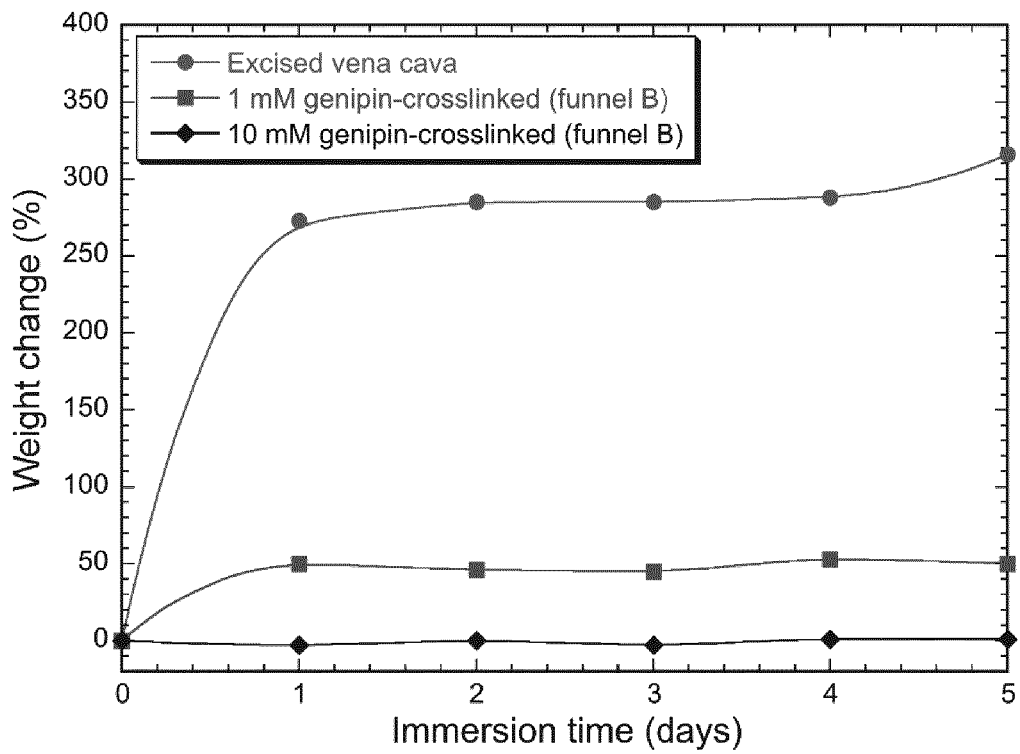
FIG. 20 is a graph showing percentage change in weight over a 5 day period for crosslinked tube samples and excised vena cava.

FIG. 20 is a graph showing percentage change in weight over a 5 day period for crosslinked tube samples and excised vena cava.

As expected, uncrosslinked samples of densified collagen tube swelled significantly when transferred from PBS to 100 mM acetic acid solution and dissolved within 2 h (FIG. 19). However, once crosslinked with genipin, this dissolution behaviour was prevented. 1 mM genipin was sufficient to prevent the dissolution of the tubes, which underwent only limited swelling. Crosslinking with 10 mM genipin eliminated the swelling of the tubes entirely, as shown over several days (FIG. 20). These tubes were compared to excised vena cava samples which, while not dissolving in acid, underwent a high degree of swelling over several days.

Section H—Generation of Densified Collagen Tubes with Two Distinct Cell Domains

Disease modelling applications may require the formation of a densified collagen tube with two distinct regions consisting of two different cell types (e.g. two different types of smooth muscle cell). Thus, tubes were manufactured casting half the precursor solution with one cell type, and casting the second half of the precursor solution with the second cell type.

Figure 21:
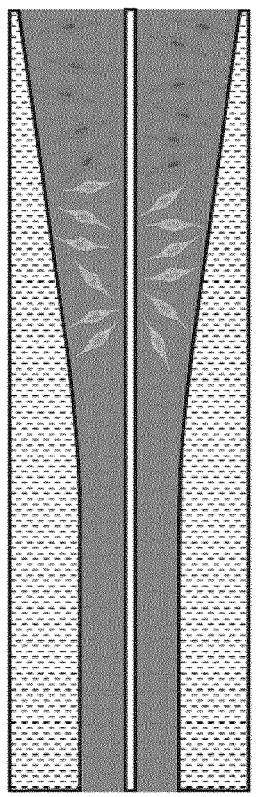
FIG. 21 is a schematic of a bulk cell seeding process.

FIG. 21 is a schematic of a bulk cell seeding process, showing the position of GFP and RFP HUVECs in undensified collagen gel (the gel casting material). Cells from each sub-population were maintained in place by the high viscosity of the precursor gel solution prior to the gelation process.

Figure 22:
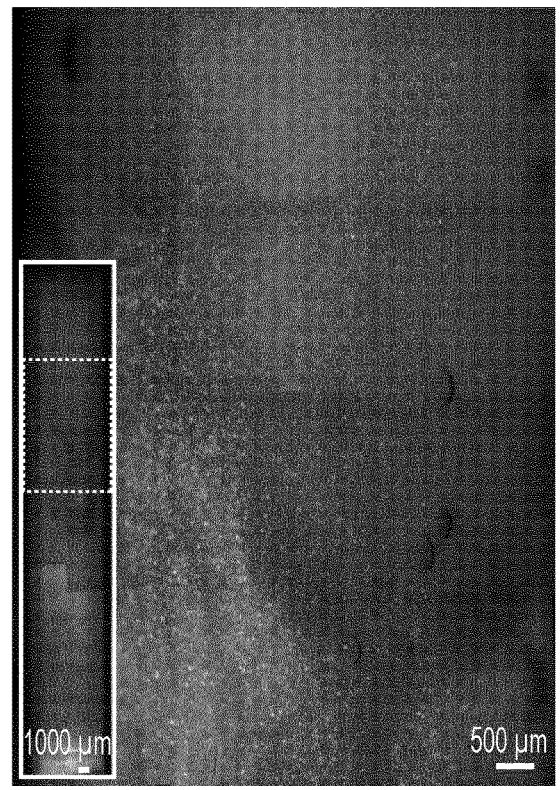
FIG. 22 is a microscopy image of green and red fluorescently labelled HUVECs show two distinct cell domains in the axial direction in a densified collagen tube. Inset shows the whole collagen tube.

FIG. 22 is a microscopy image of green and red fluorescently labelled HUVECs show two distinct cell domains in the axial direction in a densified collagen tube. Inset shows the whole collagen tube.

Figure 23:
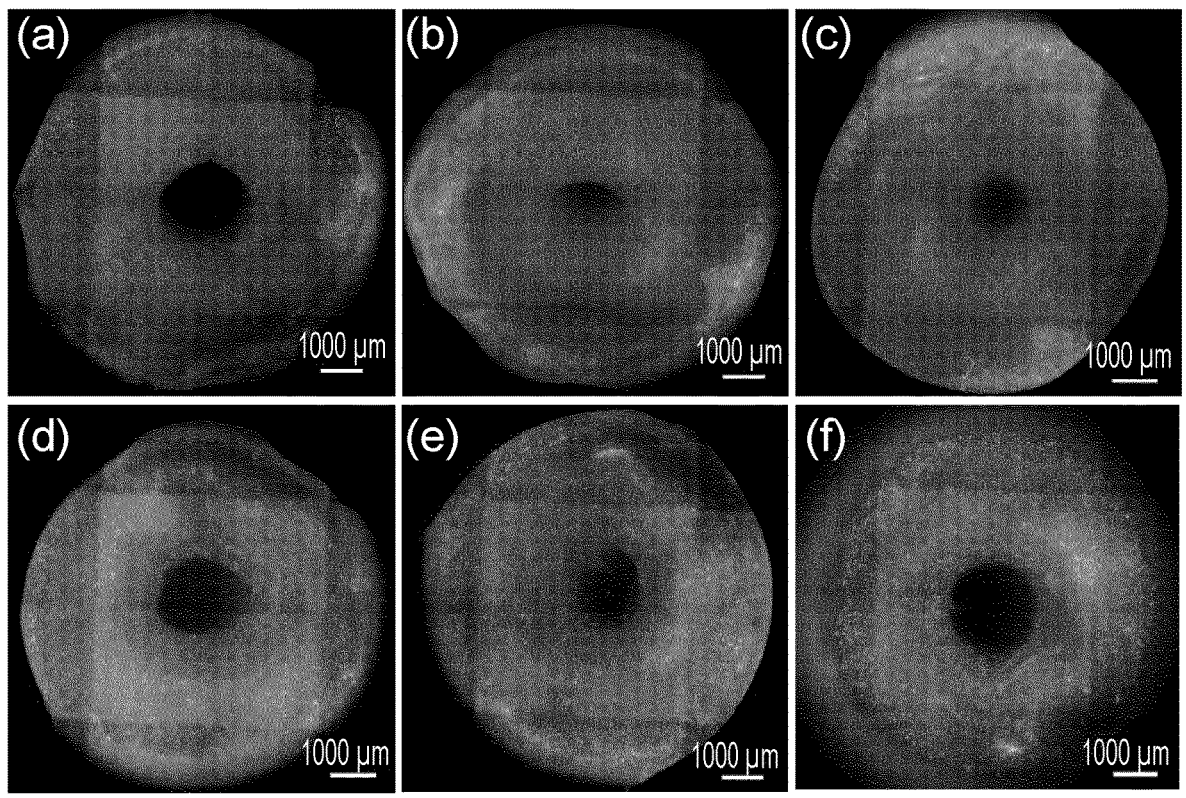
FIGS. 23 (a)-(f) are cross-sectional image samples moving down the densified collagen tube shown in FIG. 22.

FIGS. 23 (a)-(f) are cross-sectional image samples moving down the densified collagen tube, showing transition from RFP HUVECs to GFP HUVECs. The funnel volume elements of undensified collagen gel mapped into the cylindrical densified collagen tube such that the top group of HUVECs formed a domain inside the bottom group of HUVECs, wrapping around the lumen, near the boundary between the cell domains. In other words, due to the densification process, RFP HUVECs are transformed from the top of the gel to wrap around the lumen, even in the GFP HUVEC region of the tube. The particular mapping of volume elements from the funnel into the final cylindrical form is non-trivial; elements near the central rod are drawn down inside the surrounding gel due to the shape of the funnel.

REFERENCES

[1] Langer, Robert, et al. "Advances in tissue engineering." *Journal of Ped. Surgery* 51.1 (2016): 8-12.

[2] Sampaziotis, Fotios, et al. "Reconstruction of the mouse extrahepatic biliary tree using primary human extrahepatic cholangiocyte organoids." *Nature medicine* 23.8 (2017): 954.

[3] Hori, Y., et al. "Tissue engineering of the small intestine by acellular collagen sponge scaffold grafting." *The International journal of artificial organs* 24.1 (2001): 50-54.

[4] Grikscheit, Tracy C., et al. "Tissue-engineered large intestine resembles native colon with appropriate in vitro physiology and architecture." *Annals of surgery* 238.1 (2003): 35.

[5] Poghosyan, T., et al. "Esophageal tissue engineering: Current status and perspectives." *Journal of visceral surgery* 153.1 (2016): 21-29.

[6] Atala, Anthony. "Tissue engineering for the replacement of organ function in the genitourinary system." *American Journal of Transplantation* 4 (2004): 58-73.

[7] O'Leary, Cian, et al. "Respiratory tissue engineering: current status and opportunities for the future." *Tissue Engineering Part B: Reviews* 21.4 (2015): 323-344.

[8] Seifu, Dawit G., et al. "Small-diameter vascular tissue engineering." *Nature Reviews Cardiology* 10.7 (2013): 410.

[9] Huang, Angela H., and Laura E. Niklason. "Engineering of arteries in vitro." *Cellular and Molecular Life Sciences* 71.11 (2014): 2103-2118.

[10] Wangensteen, Kirk J., and Loree K. Kalliainen. "Collagen tube conduits in peripheral nerve repair: a retrospective analysis." *Hand* 5.3 (2010): 273-277.

[11] R. Williams, et al. "New metrics for the Lancet Standing Commission on Liver Disease in the UK" *The Lancet* 389.10083: 2053-2080, (2017).

[12] K. F. Murray and R. L. Carithers, "AASLD practice guidelines: evaluation of the patient for liver transplantation" *Hepatology*, vol. 41, no. 6, pp. 1407-1432, (2005).

[13] A. I. Skaro, et al., "The impact of ischemic cholangiopathy in liver transplantation using donors after cardiac death: the untold story" *Surgery*, vol. 146, no. 4, pp. 543-553, (2009).

[14] Justin, Alexander W., et al. "Advances in the generation of bioengineered bile ducts." *Biochimica et Biophysica Acta (BBA)-Molecular Basis of Disease* 1864.4 (2018): 1532-1538.

[15] Macchiarini, Paolo, et al. "Clinical transplantation of a tissue-engineered airway." *The Lancet* 372.9655 (2008): 2023-2030.

[16] Ghezzi, Chiara E., et al. "Immediate production of a tubular dense collagen construct with bioinspired mechanical properties." *Acta biomaterialia* 8.5 (2012): 1813-1825.

[17] Loy, Caroline, et al. "Rotation-based technique for the rapid densification of tubular collagen gel scaffolds." *Biotechnology journal* 11.12 (2016): 1673-1679.

[18] L'Heureux, Nicolas, et al. "Human tissue-engineered blood vessels for adult arterial revascularization." *Nature medicine* 12.3 (2006): 361.

[19] Hoenig, Michel R., et al. "Tissue-engineered blood vessels: alternative to autologous grafts?." *Arteriosclerosis, thrombosis, and vascular biology* 25.6 (2005): 1128-1134.

[20] Quint, Clay, et al. "Decellularized tissue-engineered blood vessel as an arterial conduit." *Proceedings of the National Academy of Sciences* (2011): 201019506.

[21] Boland, Eugene D., et al. "Electrospinning collagen and elastin: preliminary vascular tissue engineering." *Front Biosci* 9.1422 (2004): e32.

[22] Nakamura, Tasuo, et al. "Experimental study on the regeneration of peripheral nerve gaps through a polyglycolic acid-collagen (PGA-collagen) tube." *Brain Research* 1027.1-2 (2004): 18-29.

[23] Micol, Lionel A., et al. "High-density collagen gel tubes as a matrix for primary human bladder smooth muscle cells." *Biomaterials* 32.6 (2011): 1543-1548.

[24] Brown, Robert A., et al. "Ultrarapid engineering of biomimetic materials and tissues: Fabrication of nano- and microstructures by plastic compression." *Ad. Functional Materials* 15.11 (2005): 1762-1770.

[25] Voytik-Harbin, Sherry L., et al. "Collagen compositions and methods of use." U.S. patent application Ser. No. 15/851,732, published 5 Jul. 2018.

[26] Huc, Alain, and Rene Gimeno. "Process for the preparation of collagen tubes." U.S. Pat. No. 4,814,120. 21 Mar. 1989.

[27] Kemp, Paul D., et al. "Collagen constructs." U.S. Pat. No. 5,256,418. 26 Oct. 1993.

[28] Rhee, Woonza, and Kimberly McCullough. "Collagen-polymer tubes for use in vascular surgery." U.S. Pat. No. 5,292,802. 8 Mar. 1994.

[29] Song, H-H. Greco, et al. "Vascular tissue engineering: progress, challenges, and clinical promise." *Cell stem cell* 22.3 (2018): 340-354.

[30] Martin, Laura Y., et al. "Tissue engineering for the treatment of short bowel syndrome in children." *Pediatric research* 83.1-2 (2018): 249.

[31] Udelsman, Brooks, Douglas J. Mathisen, and Harald C. Ott. "A reassessment of tracheal substitutes—a systematic review." *Annals of cardiothoracic surgery* 7.2 (2018): 175.

[32] Goh, Cindy Siaw-Lin, et al. "Large animal models for long-segment tracheal reconstruction: a systematic review." *Journal of Surgical Research* 231 (2018): 140-153.

[33] Arakelian, Lousineh, et al. "Esophageal tissue engineering: from bench to bedside." *Annals of the New York Academy of Sciences* 1434.1 (2018): 156-163.

[34] Justin, Alexander W., et al. "Multi-casting approach for vascular networks in cellularized hydrogels." *Journal of The Royal Society Interface* 13.125 (2016): 20160768.

[35] Golden, Andrew P., and Joe Tien. "Fabrication of microfluidic hydrogels using molded gelatin as a sacrificial element." *Lab on a Chip* 7.6 (2007): 720-725.

[36] Wimmer, Reiner A., et al. "Human blood vessel organoids as a model of diabetic vasculopathy." *Nature* (2019)

[37] McCoy, Michael G., et al. "Collagen Fiber Orientation regulates 3D Vascular Network Formation and Alignment." *ACS Biomaterials Science & Engineering* 4.8 (2018): 2967-2976.

[38] Chwalek, Karolina, et al. "Glycosaminoglycan-based hydrogels to modulate heterocellular communication in in vitro angiogenesis models." *Scientific reports* 4 (2014): 4414.

The invention claimed is:

1. A method of making a tissue equivalent tubular scaffold comprising:
   providing a casting chamber comprising an elongate mould portion having a closed end, wherein at least part of the closed end of the elongate mould portion of the casting chamber is porous;
   providing a lumen template axially disposed within the elongate mould portion;
   at least partly filling the casting chamber with a gel casting material comprising a fluid phase, such that a portion of the lumen template extends above the casting material; and
   allowing axial flow of the fluid phase of the gel casting material out of the porous end part of the elongate mould portion, thereby densifying gel casting material within the elongate mould portion to form the tissue equivalent tubular scaffold.

2. The method according to claim 1 wherein gel casting material is a hydrogel or an alcogel comprising a matrix of fibres or fibrils.

3. The method according to claim 2 wherein the gel casting material comprises one or more of silk, fibrin, fibronectin, laminin, elastin, collagen, glycoproteins, polysaccharides, polylactones, inorganic polymers and carbon nanotubes.

4. The method according to claim 3 wherein the gel casting material comprises a collagen hydrogel.

5. The method according to claim 1 including a step of contacting the porous end part of the elongate mould portion with an absorbent medium to cause flow of the fluid phase of the casting material out of the porous end part of the elongate mould portion.

6. The method according to claim 1 wherein the elongate mould portion has an average inner diameter of greater than 2 mm, optionally wherein the average inner diameter of the elongate mould portion is between 2 mm and 40 mm.

7. The method according to claim 1 wherein the casting chamber further comprises a reservoir portion fluidly connected to the elongate mould portion, optionally wherein the reservoir portion is funnel-shaped.

8. The method according to claim 1 wherein the porous end part of the elongate mould portion has an average pore size of from 0.025 µm to 5 µm.

9. The method according to claim 1 wherein the porous end part of the elongate mould portion is provided by one or more porous membranes.

10. The method according to claim 9 wherein the porous end part of the elongate mould portion is provided by two or more different porous membranes, optionally wherein the porous end part of the elongate mould portion is provided by a combination of both a hydrophilic and a hydrophobic membrane.

11. The method according to claim 1 wherein the lumen template comprises a rod, or a bifurcated rod.

12. The method according to claim 1 wherein the lumen template is disposed to be substantially perpendicular to the porous end part of the elongate mould portion, and optionally is disposed centrally within the elongate mould portion.

13. The method according to claim 1, wherein after the step of at least partly filling the casting chamber, and before the step of allowing axial flow of the fluid phase of the casting material out of the casting chamber, the method further including a step of covering the mould to substantially prevent evaporation of the fluid phase of the gel from within the casting chamber.

14. The method according to claim 1 wherein the lumen template and/or one or more walls of the elongate mould portion are provided with a patterned surface comprising a plurality of surface features.

15. The method according to claim 14, wherein the method further comprises a step of forming a patterning layer providing the patterned surface on the lumen template and/or one or more walls of the elongate mould portion, optionally wherein the patterning layer comprises one or more of a gelatin gel, a calcium alginate gel, or a methylcellulose gel.

16. The method according to claim 15, wherein after densification of the solid phase of the gel casting material to form the tissue equivalent tubular scaffold, the method comprises a further step of heating or cooling one or more of the mould, the lumen template and/or the tissue equivalent tubular scaffold to thereby liquefy and remove the patterning layer.

17. The method according to claim 1 including a step of encapsulating cells within the casting material prior to densification of the casting material, optionally wherein the cells comprise two or more different types of cell.

18. The method according to claim 1 including a further step of seeding the tissue equivalent tubular scaffold with cells.

19. The method according to claim 1, wherein the method includes a crosslinking step.

20. The method according to claim 19 wherein the crosslinking step comprises:
   (i) adding one or more cross-linking agents to the gel casting material; and/or
   (ii) crosslinking the tissue equivalent tubular scaffold after densification by exposure to a suitable cross-linking agent.

* * * * *